(12) United States Patent
Zamloot et al.

(10) Patent No.: US 11,370,791 B2
(45) Date of Patent: Jun. 28, 2022

(54) SOLID POLYMORPHS OF A FLNA-BINDING COMPOUND AND ITS HYDROCHLORIDE SALTS

(71) Applicant: Pain Therapeutics, Inc., Austin, TX (US)

(72) Inventors: Michael Zamloot, Austin, TX (US); Lindsay Burns Barbier, Austin, TX (US); Shawn Anthony Kucera, Cedar Park, TX (US)

(73) Assignee: CASSAVA SCIENCES, INC., Austin, TX (US)

(*) Notice: Subject to any disclaimer, the term of this patent is extended or adjusted under 35 U.S.C. 154(b) by 0 days.

(21) Appl. No.: 16/798,041

(22) Filed: Feb. 21, 2020

(65) Prior Publication Data

US 2020/0270250 A1    Aug. 27, 2020

Related U.S. Application Data

(60) Provisional application No. 62/808,609, filed on Feb. 21, 2019.

(51) Int. Cl.
*C07D 471/10* (2006.01)

(52) U.S. Cl.
CPC ........ *C07D 471/10* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,560,468 B2 | 7/2009 | Sundermann et al. | |
| 8,614,324 B2 * | 12/2013 | Burns Barbier | ....... A61K 31/54 546/19 |
| 8,653,068 B2 | 2/2014 | Barbier et al. | |
| 9,354,223 B2 | 5/2016 | Wang et al. | |
| 9,433,604 B2 | 9/2016 | Wang et al. | |
| 9,500,640 B2 | 11/2016 | Wang et al. | |
| 10,017,736 B2 | 7/2018 | Wang et al. | |
| 10,222,368 B2 | 3/2019 | Wang et al. | |
| 10,760,052 B2 | 9/2020 | Wang et al. | |
| 2013/0012434 A1 | 6/2013 | Wong et al. | |
| 2015/0148318 A1 | 5/2015 | Wang et al. | |
| 2016/0266149 A1 | 9/2016 | Wang et al. | |

OTHER PUBLICATIONS

Feliu et al., ARKIVOC 2007, (iv), 65-72.
International Search Report for PCT/US2020/019305 (WO 2020172584).
Written Opinion of the International Searching Authority for PCT/US2020/019305.

* cited by examiner

*Primary Examiner* — Craig D Ricci
(74) *Attorney, Agent, or Firm* — Husch Blackwell LLP

(57) ABSTRACT

The preparation and properties of crystalline polymorphs and solvates of 1-benzyl-8-methyl-1,4,8-triazaspiro-[4.5]-decan-2-one free base and of the mono- and dihydrochloride salts and solvates thereof are disclosed, as is an amorphous polymorph of the dihydrochloride. A pharmaceutical composition containing one or more polymorphs and a method of using that composition are also disclosed.

9 Claims, 12 Drawing Sheets

SOLID POLYMORPHS OF A FLNA-BINDING COMPOUND AND ITS HYDROCHLORIDE SALTS

CROSS-REFERENCE TO RELATED APPLICATION

This application claims priority to U.S. application Ser. No. 62/808,609, filed on Feb. 21, 2019, whose disclosures are incorporated herein by reference.

TECHNICAL FIELD

The present invention contemplates a solid polymorph of 1-benzyl-8-methyl-1,4,8-triazaspiro-[4.5]-decan-2-one, a compound that binds tightly to the protein filamin-A (FLNA), or a polymorph of a mono- or di-hydrochloride salt of that compound.

BACKGROUND ART

1-Benzyl-8-methyl-1,4,8-triazaspiro[4.5]-decan-2-one, whose structural formula is shown below,

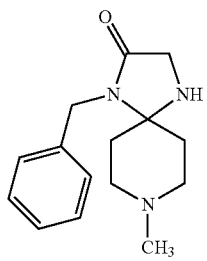

is also known in the art as Compound C0105 and C0105M, and specifically binds to the protein filamin-A (FLNA). A competition (displacement) curve for the inhibition of tritium-labeled naloxone ([$^3$H]NLX) binding by Compound C0105 in a membrane preparation from A7 cells or SK-N-MC cells following a procedure discussed in Wang et al., *PlosOne* 3(2):e1554 (2008) exhibits an $EC_{50}$ value in the range of about $10^{-12}$ to $10^{-13}$ M for the higher affinity binding site of the two such sites identified. Using a N-biotinylated pentapeptide (Bn-VAKGL; SEQ ID NO: 1) present in the sequence of FLNA in place of that membrane preparation provides an $EC_{50}$ value of similar magnitude to that obtained with the membrane preparation and indicates the presence of a single affinity site in that pentamer.

Compound C0105 is disclosed, synthesized and claimed in U.S. Pat. No. 8,653,068. Preparation of a pharmaceutically acceptable salt of Compound C0105 was also disclosed, although no such salts were specifically prepared, and the compound was isolated and used only as an orange/yellow gum, which by HPLC and $^1$H-NMR was found to be about 86 to about 97% pure, depending on the preparation used.

Contacting appropriate cells with Compound C0105 can, inter alia, reduce an inflammatory response (U.S. Pat. No. 8,653,068), inhibit phosphorylation of the tau protein and formation of tau-containing plaques (U.S. Pat. No. 10,017, 736), and inhibit the growth of certain cancer cells that contain an enhanced amount relative to non-cancerous cells of one or more of phosphorylated mTOR, Akt1, ERK2 and serine2152-phosphorylated filaminA as disclosed in U.S. Pat. No. 9,433,604, and for the treatment of Alzheimer's disease as discussed in U.S. Pat. No. 10,222,368 and in Wang et al., *J Prev Alz Dis,* 2020, published on line on Feb. 7, 2020. Compound C0105 can be used in an assay for diagnosis of Alzheimer's disease (AD) in a living patient, for determining the effectiveness of a therapy for AD, and for treating AD as are taught in U.S. Pat. Nos. 9,354,223, 9,500,640, and 10,222,368, respectively.

In the formulation of a pharmaceutical composition of an active pharmaceutical ingredient (API, compound or drug), it can be important for the drug substance to be in a form in which it can be conveniently handled and processed. This can be of importance, not only from the point of view of obtaining a commercially viable manufacturing process, but also from the point of subsequent manufacture of a pharmaceutical formulation comprising the active compound. A gum is not such a conveniently handled and processed form.

Chemical stability, solid state stability, and shelf life of the active ingredients are also important factors. The drug substance, and a composition containing it, should be capable of being effectively stored over appreciable periods of time without exhibiting a significant change in the active component's physico-chemical characteristics (e.g., its chemical composition, density, hygroscopicity and solubility).

Moreover, it can also be important to be able to provide a drug in a form that is as pure as possible. Amorphous materials as compared to crystalline materials can present significant problems in this regard. For example, such materials are typically more difficult to handle and to formulate than are crystalline materials, provide unreliable solubilities, and are often found to be unstable and chemically impure. The skilled person understands that if an active pharmaceutical ingredient (API) can be readily obtained in a stable crystalline form, the above problems can be greatly alleviated if not solved.

Thus, in the manufacture of commercially viable and pharmaceutically acceptable drug compositions, it is desirable, wherever possible, to provide the API in a substantially crystalline, and stable, form. It is to be noted, however, that this goal is not always achievable. Indeed, it is typically not possible to predict, from molecular structure alone, what the crystallization and post crystallization behavior of a compound will be, and such behaviors can often only be determined empirically.

BRIEF SUMMARY OF THE INVENTION

The present invention contemplates a solid polymorph of 1-benzyl-8-methyl-1,4,8-triazaspiro-[4.5]-decan-2-one, its solvates and a polymorph of the mono- and dihydrochloride salt of that compound as well as a solvate thereof.

In one aspect, a solid form of a compound of Formula III and a pharmaceutically acceptable

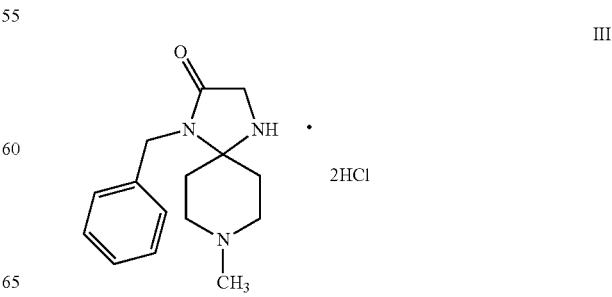

solvate whose X-ray powder diffraction pattern exhibits characteristic peaks that define a
  a) a crystalline monohydrate Form 1, characterized by:
    an X-ray powder diffraction pattern having at least 1 peak selected from 8.0, 13.0, 13.8, 19.1 and 20.2 2θ±0.2° 2θ; or
    an X-ray powder diffraction pattern substantially similar to FIG. 1;
  b) a Crystalline monohydrate Form 2, characterized by:
    an X-ray powder diffraction pattern having at least 1 peak selected from 9.9, 11.9, 13.2, 14.2, 15.8, 20.0 and 20.4 2θ±0.2° 2θ; or
    an X-ray powder diffraction pattern substantially similar to FIG. 2;
  c) a Crystalline dimethylacetamide solvate Form 3, characterized by:
    an X-ray powder diffraction pattern having a peak at 5.5 2θ±0.2° 2θ; or
    an X-ray powder diffraction pattern substantially similar to FIG. 3;
  (d) an amorphous Form 4, characterized by:
    an X-ray powder diffraction pattern substantially similar to FIG. 4; and
  (e) a Crystalline monohydrate Form 5, characterized by:
    an X-ray powder diffraction pattern having a peak at 22.4 2θ±0.2° 2θ; or
    an X-ray powder diffraction pattern substantially similar to FIG. 5.

A crystalline form of the compound of Formula II selected from

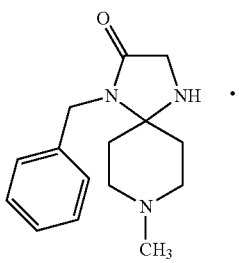

II (a) a Crystalline Form 1 characterized by:
    an X-ray powder diffraction pattern having at least one peak selected from 12.4, 20.5, 21.7 and 25.5 2θ±0.2° 2θ; or
    an X-ray powder diffraction pattern substantially similar to FIG. 6;
  (b) a Crystalline Form 2 characterized by:
    an X-ray powder diffraction pattern having at least one peak selected form 10.5, 13.8 and 22.7 2θ±0.2° 2θ; or
    an X-ray powder diffraction pattern substantially similar to FIG. 7; or
  (c) a Crystalline Form 3 characterized by:
    an X-ray powder diffraction pattern having at least one peak selected from 13.6, 15.8, 20.8, 22.0 and 27.2 2θ±0.2° 2θ; or
    an X-ray powder diffraction pattern substantially similar to FIG. 8; and
  (d) a Crystalline Form 4 characterized by:
    an X-ray powder diffraction pattern having at least one peak selected from 11.2, 18.0 and 20.0 2θ±0.2° 2θ; or
    an X-ray powder diffraction pattern substantially similar to FIG. 9.

A crystalline form of the compound of Formula I that is selected from

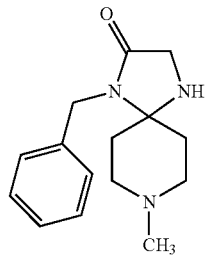

I a) a Crystalline Form 1, characterized by:
    an X-ray powder diffraction pattern having at least one peak selected from 24.1, 26.3 and 27.3 2θ±0.2° 2θ; or
    an X-ray powder diffraction pattern substantially similar to FIG. 10;
  b) a Crystalline Form 2, characterized by:
    an X-ray powder diffraction pattern having at least one peak selected from 13.1 and 16.8 2θ±0.2° 2θ; or
    an X-ray powder diffraction pattern substantially similar to FIG. 11; and
  c) a Crystalline Form 3, characterized by:
    an X-ray powder diffraction pattern having at least one peak selected from 10.1, 14.1 and 19.3 2θ±0.2° 2θ; or
    an X-ray powder diffraction pattern substantially similar to FIG. 12.

Another aspect of the invention contemplates a pharmaceutical composition that comprises an above crystalline or amorphous form of a compound of one or more of Formulas I, II or III that can be dissolved or is dispersed in a physiologically tolerable carrier or diluent in an amount effective for one or more of reducing or inhibiting tau protein phosphorylation, inhibiting the interaction of FLNA with α7nAChR and TLR4, inhibiting the interaction of Aβ$_{42}$ with α7nAChR, inhibiting the growth of cancer cells as discussed above, reducing one or both of pain and inflammation, or treating and/or assaying for Alzheimer's Disease in a living patient.

A method of reducing or inhibiting tau protein phosphorylation, inhibiting the interaction of FLNA with α7nAChR and TLR4, inhibiting the interaction of Aβ$_{42}$ with α7nAChR, inhibiting the growth of cancer cells, reducing one or both of pain and inflammation, or treating and/or assaying for Alzheimer's Disease in a living patient is contemplated that comprises administering to that host mammal an above-described pharmaceutical composition.

BRIEF DESCRIPTION OF THE DRAWINGS

In the drawings forming a portion of this disclosure.

Figure 1:
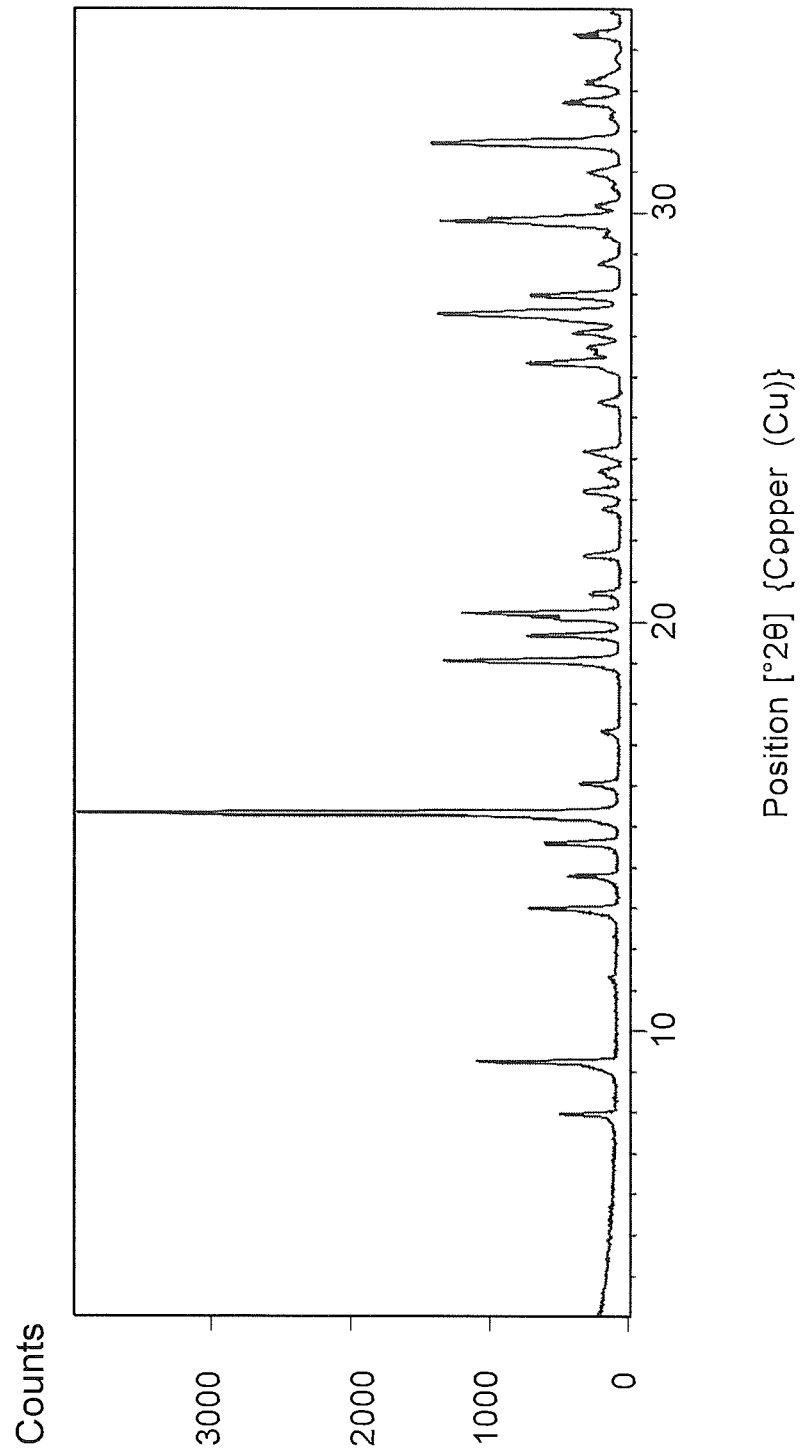
FIG. 1 is an X-ray powder diffraction pattern for crystalline 1-benzyl-8-methyl-1,4,8-triazaspiro-[4.5]-decan-2-one dihydrochloride monohydrate, Crystalline Form 1.

The present invention has several benefits and advantages.

One benefit is that it provides the API in a plurality of crystalline and stable forms.

An advantage of the invention is that one of those crystalline and stable forms of the dihydrochloride of 1-benzyl-8-methyl-1,4,8-triazaspiro-[4.5]-decan-2-one is particularly useful in the preparation of a solid oral composition.

Another benefit of the invention is that it provides a particularly stable hydrated dihydrochloride salt.

Another advantage of the invention is that it provides an amorphous polymorph of the dihydrochloride salt.

Still other benefits and advantages will be apparent to the skilled worker from the description and claims that follow.

DETAILED DESCRIPTION OF THE INVENTION

The present invention contemplates a polymorphic form of a compound, 1-benzyl-8-methyl-1,4,8-triazaspiro[4.5]-decan-2-one, whose structural Formula I is shown below, as well as polymorphs of

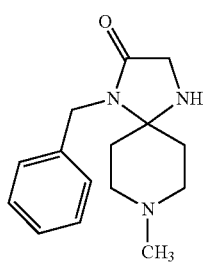 [SMILES: CN1CCC2(CC1)NCC(=O)N2Cc1ccccc1]

I its mono- and dihydrochloride salts, and a pharmaceutically acceptable solvate thereof (a pharmaceutically acceptable solvatomorph). That compound of structural Formula I is also known in the art as Compound C0105 (also C0105M). Those polymorphs of the free base, mono- or dihydrochloride salt or a solvate thereof are identified from the peaks in their X-ray powder diffraction (XRPD) spectra.

Polymorphs of solid forms of the molecule are usually defined by one or more characteristic peaks expressed in scattering angle position values of two-theta (° 2θ), ±0.2°. Further characteristic data for each polymorphic form include the d-spacing that is a measure of the distance between planes of molecules in a crystalline form that relate to a particular ° 2θ peak, and the relative intensity of each of the identified peaks as a percentage of the peak of greatest intensity.

A characteristic scattering pattern (diffractogram) that identifies a particular crystalline polymorph can contain only a single peak that is unique to that particular polymorph. It is deemed better practice to utilize 3 to 5 peaks, and more preferably, an excess of 5 peaks are used to identify a particular polymorph. Therefore, in cases where only 1 or 2 marker peaks are unique to a particular polymorph, and one or more other peaks are shared (overlap) with peaks produced by another polymorph, using the unique peak data with data for 1 to 5 peaks that overlap can provide a definitive diffractogram for the particular polymorph.

Scattering peaks with relative intensities of at least 5% of the intensity of the most intense peak are preferably reported as members of a characteristic scattering pattern. However, in cases where few and/or lower relative intensity peaks are those observed and reported for a characteristic scattering pattern.

Characteristic two-theta positions, d-spacing and intensity percentages are provided in the tables below for twelve contemplated polymorphs of Compound C0105 as a free base and as its di-(bis-) and mono-hydrochloride salts, and solvates thereof. Each °2θ measurement in the tables below is ±0.2°, which is not shown in the tables to improve clarity in the tables. Data are typically reported up to about scattering angles of about 20 to about 30°2θ.

A minimum of one XRPD marker peak can be used to identify a particular crystalline form of a compound known to be a free base, a monohydrochloride or a dihydrochloride or a solvate thereof. Preferably at least 3 XRPD marker peaks are used, and more preferably, 5 or more further XRPD marker peaks are used when they are present in a diffractogram. As can be seen from the figures herein, the number of resolvable peaks can vary among the various crystalline forms of the free base or hydrochloride salts.

"Marker peak(s)" is used to identify an XRPD peak that is unique to the particular polymorph and can be used to identify that polymorph. The phrase "Total X-ray Powder Diffraction Pattern" is used to enumerate and the peaks that are identified in a diffractogram, whether they are marker peaks or not. The phrase "Peaks That Slightly Overlap With Other Form Peaks" are those peaks with one or more Marker peaks can be used to identify a particular polymorph.

The phrase "pharmaceutically acceptable solvate" is used to refer to a solvent molecule that forms a portion of the crystalline matrix of a contemplated polymorph. Solvates are named with the name of the solvent followed by the word "solvate", except where water is the solvate where the word "hydrate" is used. A "pharmaceutically acceptable solvate" contains a solvent that can be present in a pharmaceutical product in accordance with local or national pharmaceutical laws and regulations such as those of the FDA in the United States. Exemplary solvates thus include a hydrate, a methanol solvate, an ethanol solvate, an isopropanol solvate, dimethylacetamide solvate, and the like.

A pharmaceutical composition can be prepared by dissolving or dispersing an effective amount of a contemplated polymorph or its solvate in physiologically tolerable carrier or diluent. A "physiologically tolerable carrier or diluent" is a diluent or carrier that can be present in a pharmaceutical product in accordance with local or national pharmaceutical laws and regulations such as those of the FDA in the United States.

Polymorphs are referred to by the word "Form" followed by an Arabic numeral. Use of the numeral is only for convenience in distinguishing one polymorph from another, with no other meaning intended.

Characterization of Crystalline Forms

FIG. 1 is an X-ray powder diffraction pattern (XRPD) of crystalline 1-benzyl-8-methyl-1,4,8-triazaspiro-[4.5]-decan-2-one dihydrochloride monohydrate, Crystalline Form 1 was obtained using a Philips Pananalytical X'Pert powder Materials Research Diffractometer (MRD) machine in over the scan range 3° to 35° 2θ with a 0.013° 2θ increment. The X-rays were generated by a copper anode operated at 40 kV and 40 mA. The wavelength of the X-rays was 1.5406 A. Table 1 lists the positions, ° 2θ±0.2° 2θ, d-spacing and relative intensity of peaks identified in the experimental XRPD pattern of FIG. 1.

The entire list of peaks, or a unique subset thereof, can be sufficient to characterize the crystalline form, as well as by an XRPD pattern substantially similar (that is, identifiable by one of ordinary skill using a characterization method, such as this one, within experimental variations) to FIG. 1. Table 2 lists peaks identified in the experimental XRPD pattern of FIG. 1 which do not overlap with peaks in the XRPD diffraction patterns of other polymorphs and which represent preferred peaks to identify the crystalline form.

TABLE 1

| Position [°2θ] | d-spacing Å | intensity in % |
|---|---|---|
| 8.0 | 11.09 | 5.2 |
| 9.2 | 9.58 | 100.0 |
| 13.0 | 6.81 | 10.8 |
| 13.8 | 6.41 | 8.1 |
| 15.4 | 5.77 | 57.3 |
| 16.1 | 5.52 | 5.4 |
| 19.1 | 4.65 | 39.8 |
| 19.7 | 4.51 | 35.1 |
| 20.2 | 4.39 | 19.7 |
| 21.7 | 4.10 | 5.9 |
| 22.8 | 3.90 | 5.2 |
| 23.2 | 3.83 | 7.3 |
| 24.2 | 3.68 | 18.5 |

Peaks presented were selected to be lower than 2 theta = 25, and % intensity greater than 5%.

TABLE 2

| Position [°2θ] | d-spacing Å | intensity in % |
|---|---|---|
| 8.0 | 11.09 | 5.2 |
| 13.0 | 6.81 | 10.8 |
| 13.8 | 6.41 | 8.1 |
| 19.1 | 4.65 | 39.8 |
| 20.2 | 4.39 | 19.7 |

Peaks presented were selected to be lower than 2 theta = 25°, and % intensity greater than 5%.

C0105 Bis-HCl Salt Monohydrate: Form 2

Figure 2:
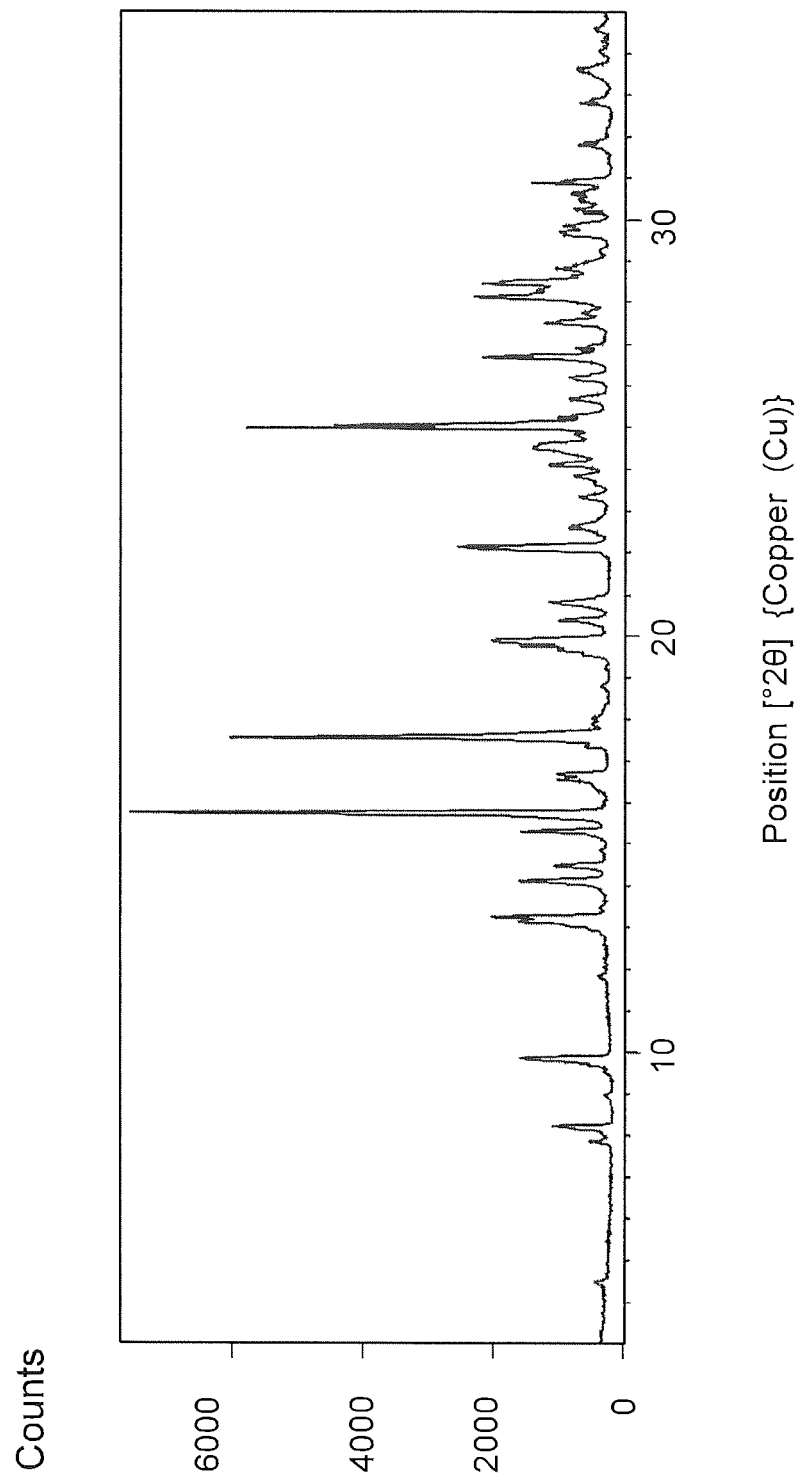
FIG. 2 is an X-ray powder diffraction (XRPD) pattern for is an X-ray powder diffraction pattern for crystalline 1-benzyl-8-methyl-1,4,8-triazaspiro-[4.5]-decan-2-one dihydrochloride monohydrate, Crystalline Form 2.

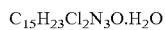 Chemical Formula:

FIG. 2 is an X-ray powder diffraction (XRPD) pattern of crystalline 1-benzyl-8-methyl-1,4,8-triazaspiro-[4.5]-decan-2-one dihydrochloride monohydrate, Crystalline Form 2 obtained as described for FIG. 1.

Table 3 lists the positions, °2θ±0.2° 2θ, d-spacing and relative intensity of peaks identified in the experimental XRPD pattern of FIG. 2. The entire list of peaks, or an unique subset thereof, can be sufficient to characterize the crystalline form, as well as by an XRPD pattern substantially similar (that is, identifiable by one of ordinary skill using a characterization method, such as this one, within experimental variations) to FIG. 2.

Table 4 lists peaks ident that do not overlap with peaks in the XRPD diffraction patterns of other polymorphs and which represent preferred peaks to identify the crystalline form.

TABLE 3

| Position [°2θ] | d-spacing Å | intensity in % |
|---|---|---|
| 8.3 | 10.622 | 32.3 |
| 9.2 | 9.62 | 10.8 |
| 9.9 | 8.89 | 91.3 |
| 10.1 | 8.77 | 18.1 |
| 13.2 | 6.71 | 100.0 |
| 14.2 | 6.24 | 7.5 |
| 14.6 | 6.08 | 18.1 |
| 15.4 | 5.75 | 22.2 |
| 15.8 | 5.61 | 18.4 |
| 17.6 | 5.04 | 29.9 |
| 18.0 | 4.94 | 9.5 |
| 20.0 | 4.45 | 23.0 |
| 20.4 | 4.35 | 12.0 |
| 20.9 | 4.24 | 9.9 |
| 22.3 | 3.99 | 20.7 |
| 23.5 | 3.79 | 11.1 |
| 24.0 | 3.71 | 17.4 |
| 24.2 | 3.68 | 24.0 |
| 24.6 | 3.62 | 7.5 |
| 24.8 | 3.59 | 29.5 |
| 25.2 | 3.54 | 19.7 |

Peaks presented were selected to be lower than 2 theta = 30, and % intensity greater than 5%.

TABLE 4

| Position [°2θ] | d-spacing Å | intensity in % |
|---|---|---|
| 9.9 | 8.89 | 91.3 |
| 11.9 | 7.42 | 4.7* |
| 13.2 | 6.71 | 100.00 |
| 14.2 | 6.24 | 7.5 |
| 15.8 | 5.61 | 18.4 |
| 20.0 | 4.45 | 23.0 |
| 20.4 | 4.35 | 12.0 |

Peaks presented were selected to be lower than 2 theta = 25, and % intensity greater than 5%, except for the * peak whose position was unique, providing for the exception.

C0105 Bis-HCl Salt DMA Solvate: Form 3

Figure 3:
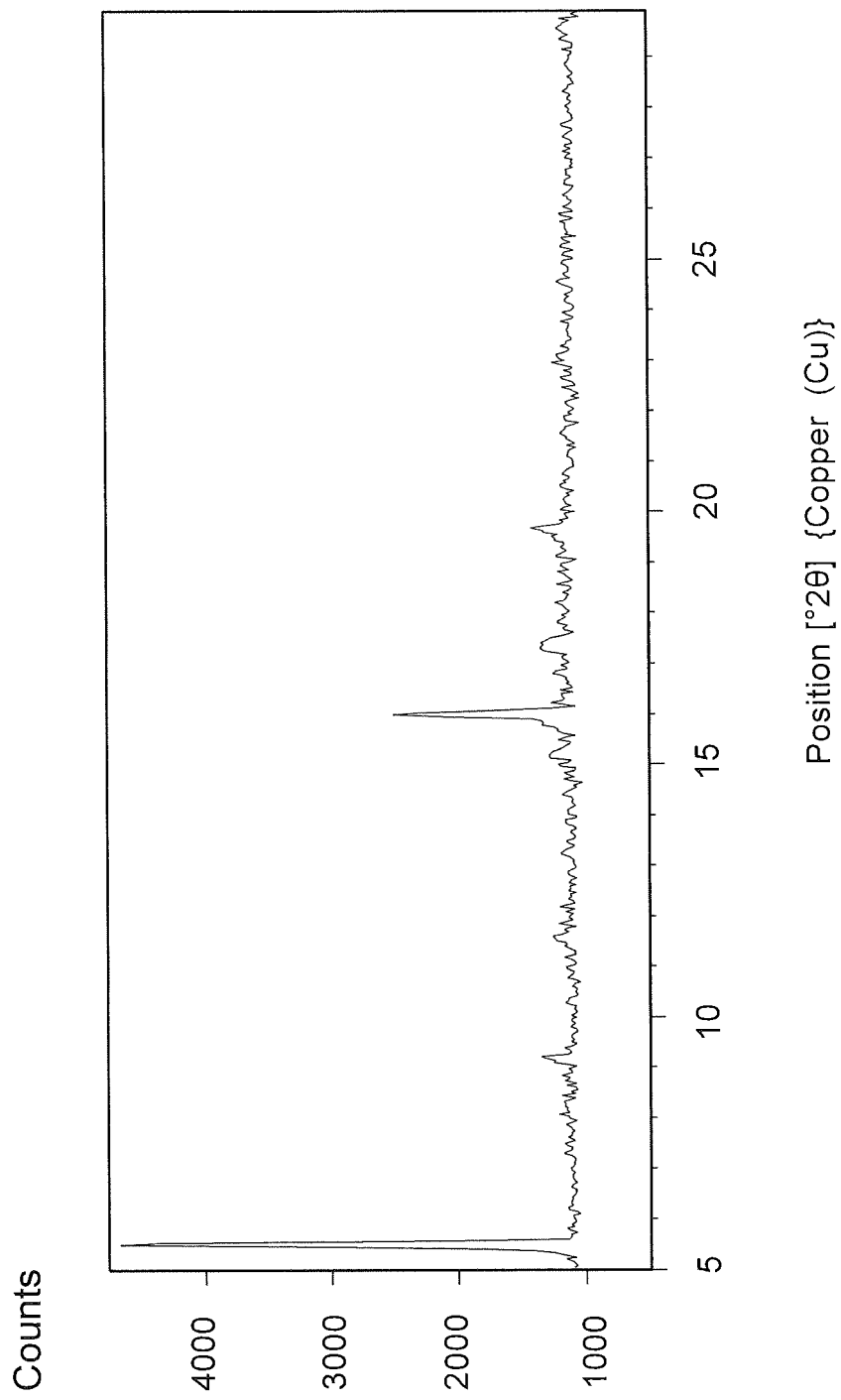
FIG. 3 is an X-ray powder diffraction (XRPD) pattern for is an X-ray powder diffraction pattern for crystalline 1-benzyl-8-methyl-1,4,8-triazaspiro-[4.5]-decan-2-one dihydrochloride dimethylacetamide solvate, Crystalline Form 3.

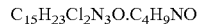 Chemical Formula:

FIG. 3 is an X-ray powder diffraction (XRPD) pattern for is an X-ray powder diffraction pattern for crystalline 1-benzyl-8-methyl-1,4,8-triazaspiro-[4.5]-decan-2-one dihydrochloride dimethylacetamide solvate, Crystalline Form 3 obtained as described for FIG. 1, except that the peaks presented are all peaks that could be detected.

Table 5 lists the positions, °2θ±0.2° 2θ, d-spacing and relative intensity of peaks identified in the experimental XRPD pattern of FIG. 3. The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 3.

Table 6 lists peaks identified in the experimental XRPD pattern of FIG. 3 which do not overlap with peaks in the XRPD diffraction patterns of other polymorphs and which represent preferred peaks to identify the crystalline form.

TABLE 5

| Position [°2θ] | d-spacing Å | intensity in % |
|---|---|---|
| 5.5 | 16.07 | 100.0 |
| 9.1 | 9.67 | 3.5 |
| 16.0 | 5.54 | 44.1 |
| 17.4 | 5.11 | 18.6 |
| 19.6 | 4.53 | 13.5 |

Peaks presented are all peaks that could be detected as the sample exhibited few peaks.

TABLE 6

| Position [°2θ] | d-spacing Å | intensity in % |
|---|---|---|
| 5.5 | 16.07 | 100.0 |

C0105 Bis-HCl Salt: Form 4-Amorphous

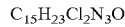  Chemical Formula: $C_{15}H_{23}Cl_2N_3O$

Figure 4:
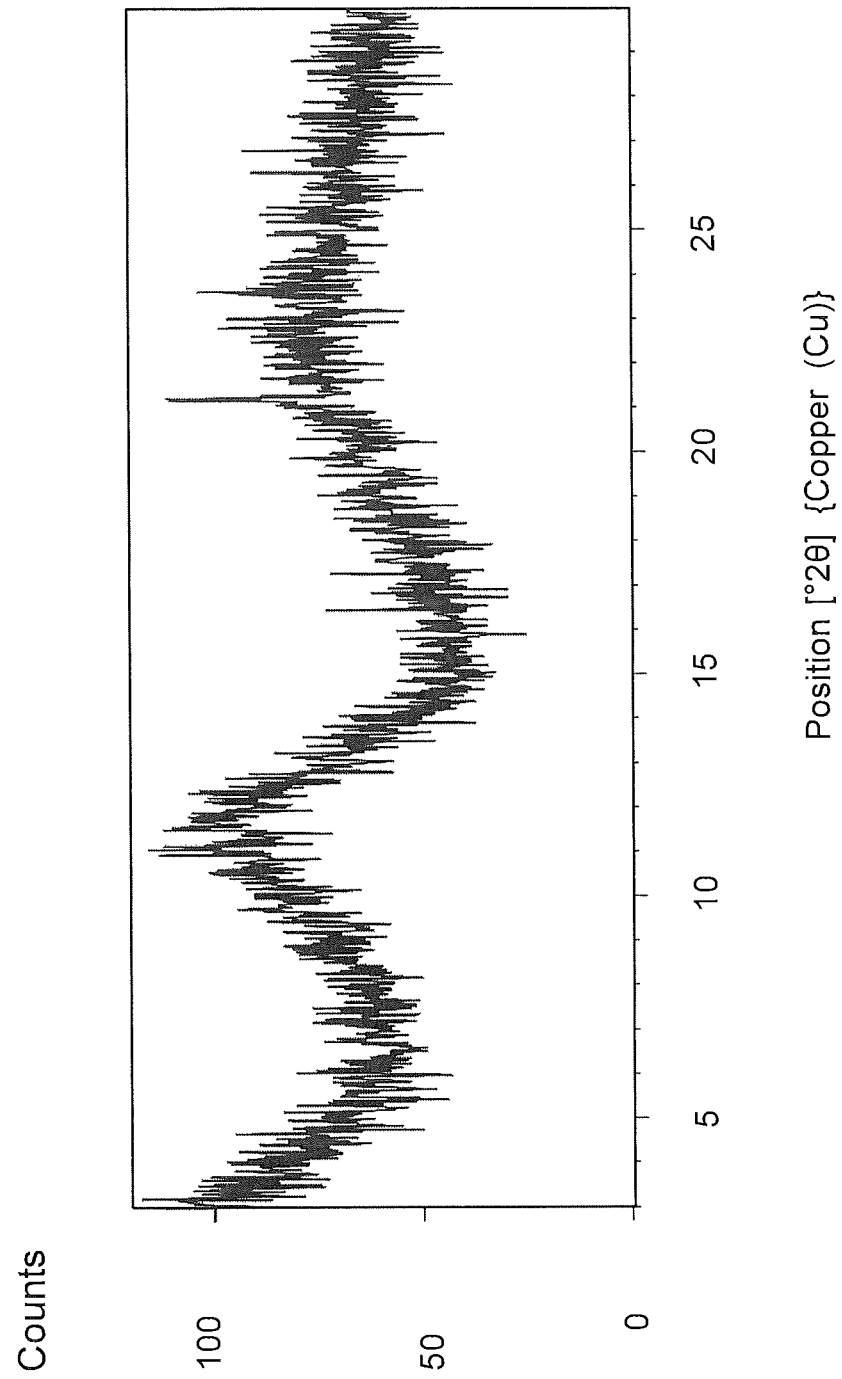
FIG. 4 is an X-ray powder diffraction (XRPD) pattern for amorphous 1-benzyl-8-methyl-1,4,8-triazaspiro-[4.5]-decan-2-one dihydrochloride, Form 4.

FIG. 4 is an X-ray powder diffraction (XRPD) pattern for amorphous 1-benzyl-8-methyl-1,4,8-triazaspiro-[4.5]-decan-2-one dihydrochloride, Form 4 obtained using a Siemens D5000 diffractometer machine over the scan range 3° to 30.0° 2θ with a 0.02° 2θ increment. The X-rays were generated by a copper anode operated at 40 kV and 40 mA. No peaks were observed indicating an amorphous solid-state form.

C0105 Bis-HCl Salt Monohydrate: Form 5

  Chemical Formula: $C_{15}H_{23}Cl_2N_3O \cdot H_2O$

Figure 5:
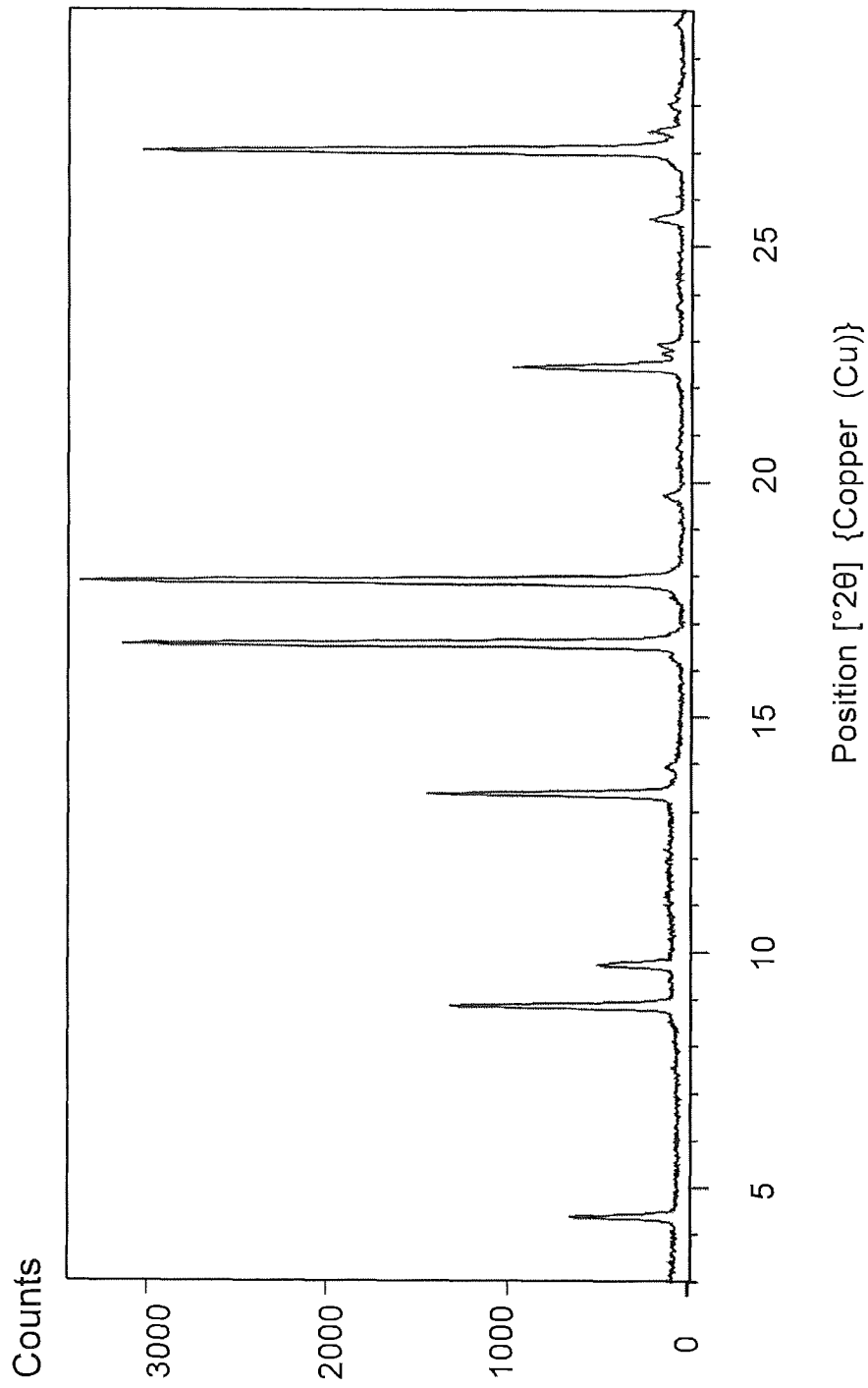
FIG. 5 is an X-ray powder diffraction (XRPD) pattern for crystalline 1-benzyl-8-methyl-1,4,8-triazaspiro-[4.5]-decan-2-one dihydrochloride monohydrate, Crystalline Form 5.

FIG. 5 is an X-ray powder diffraction (XRPD) pattern for crystalline 1-benzyl-8-methyl-1,4,8-triazaspiro-[4.5]-decan-2-one dihydrochloride monohydrate, Crystalline Form 5 obtained as described for FIG. 4, except that the peaks presented were selected to have at least 5% intensity of the most intense peak and to be lower than 2θ=30°.

Table 7 lists the positions, ° 2θ±0.2° 2θ, d-spacing and relative intensity of peaks identified in the experimental XRPD pattern of FIG. 5. The entire list of peaks, or an unique subset thereof, can be sufficient to characterize the crystalline form, as well as by an XRPD pattern substantially similar (that is, identifiable by one of ordinary skill using a characterization method, such as this one, within experimental variations) to FIG. 5.

Table 8 lists peaks identified in the experimental XRPD pattern of FIG. 5 that do not overlap with peaks in the XRPD diffraction patterns of other polymorphs and which represent preferred peaks to identify the crystalline form. Table 9 lists characteristic peaks identified in the experimental XRPD pattern of FIG. 5 that can slightly overlap with peaks in the XRPD diffraction patterns of other polymorphs.

TABLE 7

| Position [°2θ] | d-spacing Å | intensity in % |
|---|---|---|
| 4.4 | 20.20 | 17.4 |
| 8.9 | 9.98 | 36.8 |
| 9.7 | 9.08 | 12.6 |
| 13.4 | 6.63 | 40.8 |

TABLE 7-continued

| Position [°2θ] | d-spacing Å | intensity in % |
|---|---|---|
| 16.5 | 5.36 | 90.0 |
| 17.9 | 4.96 | 100.0 |
| 22.4 | 3.96 | 27.6 |
| 27.0 | 3.30 | 77.2 |
| 27.4 | 3.25 | 5.6 |

Peaks presented were selected to be lower than 2 theta = 30, and % intensity greater than 5%.

TABLE 8

| Position [°2θ] | d-spacing Å | intensity in % |
|---|---|---|
| 22.4 | 3.96 | 27.6 |

Peaks presented were selected to be lower than 2 theta = 30, and % intensity greater than 5%.

TABLE 9

| Position [°2θ] | d-spacing Å | intensity in % |
|---|---|---|
| 8.9 | 9.98 | 36.8 |
| 9.7 | 9.08 | 12.6 |
| 17.9 | 4.96 | 100.0 |

Peaks presented were selected to be lower than 2 theta = 30, and % intensity greater than 5%.

C0105 Mono-HCl Salt: Form 1

  Chemical Formula: $C_{15}H_{22}ClN_3O$

Figure 6:
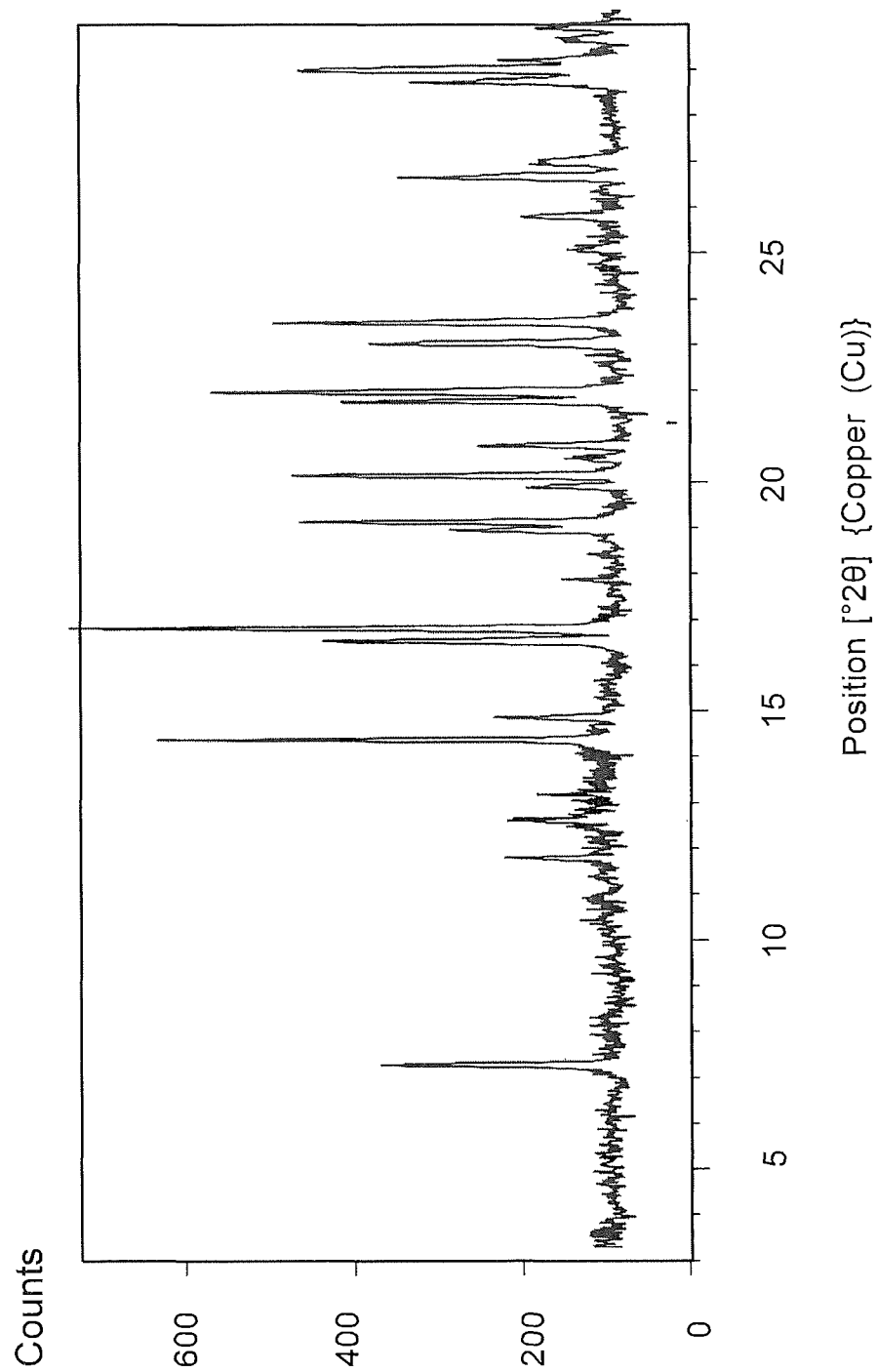
FIG. 6 is an X-ray powder diffraction pattern for crystalline 1-benzyl-8-methyl-1,4,8-triazaspiro-[4.5]-decan-2-one monohydrochloride, Crystalline Form 1.

FIG. 6 is an X-ray powder diffraction (XRPD) pattern for crystalline 1-benzyl-8-methyl-1,4,8-triazaspiro-[4.5]-decan-2-one monohydrochloride, Crystalline Form 1 obtained as described for FIG. 4, except that the peaks presented were selected to have at least 5% intensity of the most intense peak and to be lower than 2θ=30°.

Table 10 lists the positions, ° 2θ±0.2° 2θ, d-spacing and relative intensity of peaks identified in the experimental XRPD pattern of FIG. 6. The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 6.

Table 11 lists peaks identified in the experimental XRPD pattern of FIG. 6 that do not overlap with peaks in the XRPD diffraction patterns of other polymorphs and which represent preferred peaks to identify the crystalline form. Table 12 lists a characteristic peak identified in the experimental XRPD pattern of FIG. 6 that can slightly overlap with peaks in the XRPD diffraction patterns of other polymorphs.

TABLE 10

| Position [°2θ] | d-spacing Å | intensity in % |
|---|---|---|
| 7.0 | 12.64 | 43.8 |
| 11.5 | 7.68 | 27.0 |
| 12.4 | 7.17 | 25.7 |
| 14.1 | 6.29 | 89.5 |
| 14.6 | 6.08 | 23.4 |
| 16.3 | 5.45 | 53.3 |
| 16.5 | 5.37 | 100.0 |
| 17.6 | 5.04 | 5.3 |
| 18.7 | 4.76 | 31.5 |

TABLE 10-continued

| Position [°2θ] | d-spacing Å | intensity in % |
|---|---|---|
| 18.8 | 4.71 | 59.4 |
| 19.6 | 4.53 | 17.7 |
| 19.9 | 4.47 | 62.2 |
| 20.2 | 4.39 | 9.0 |
| 20.5 | 4.33 | 29.8 |
| 21.5 | 4.14 | 54.9 |
| 21.7 | 4.10 | 77.6 |
| 22.7 | 3.91 | 48.8 |
| 23.2 | 3.84 | 65.4 |
| 24.8 | 3.59 | 7.6 |
| 25.5 | 3.49 | 19.7 |
| 26.4 | 3.38 | 33.9 |
| 26.7 | 3.34 | 16.0 |
| 28.4 | 3.14 | 37.9 |
| 28.7 | 3.11 | 59.9 |
| 28.9 | 3.09 | 20.0 |
| 29.4 | 3.04 | 9.8 |
| 29.7 | 3.01 | 14.8 |

Peaks presented were selected to be lower than 2 theta = 30°, and % intensity greater than 5%.

TABLE 11

| Position [°2θ] | d-spacing Å | intensity in % |
|---|---|---|
| 12.4 | 7.17 | 25.7 |
| 20.5 | 4.33 | 29.8 |
| 21.7 | 4.10 | 77.6 |
| 25.5 | 3.49 | 19.7 |

Peaks presented were selected to be lower than 2 theta = 30°, and % intensity greater than 5%.

TABLE 12

| Position [°2θ] | d-spacing Å | intensity in % |
|---|---|---|
| 28.7 | 3.11 | 59.9 |

Peaks presented were selected to be lower than 2 theta = 30, and % intensity greater than 5%.

C0105 Mono-HCl Salt: Form 2

Figure 7:
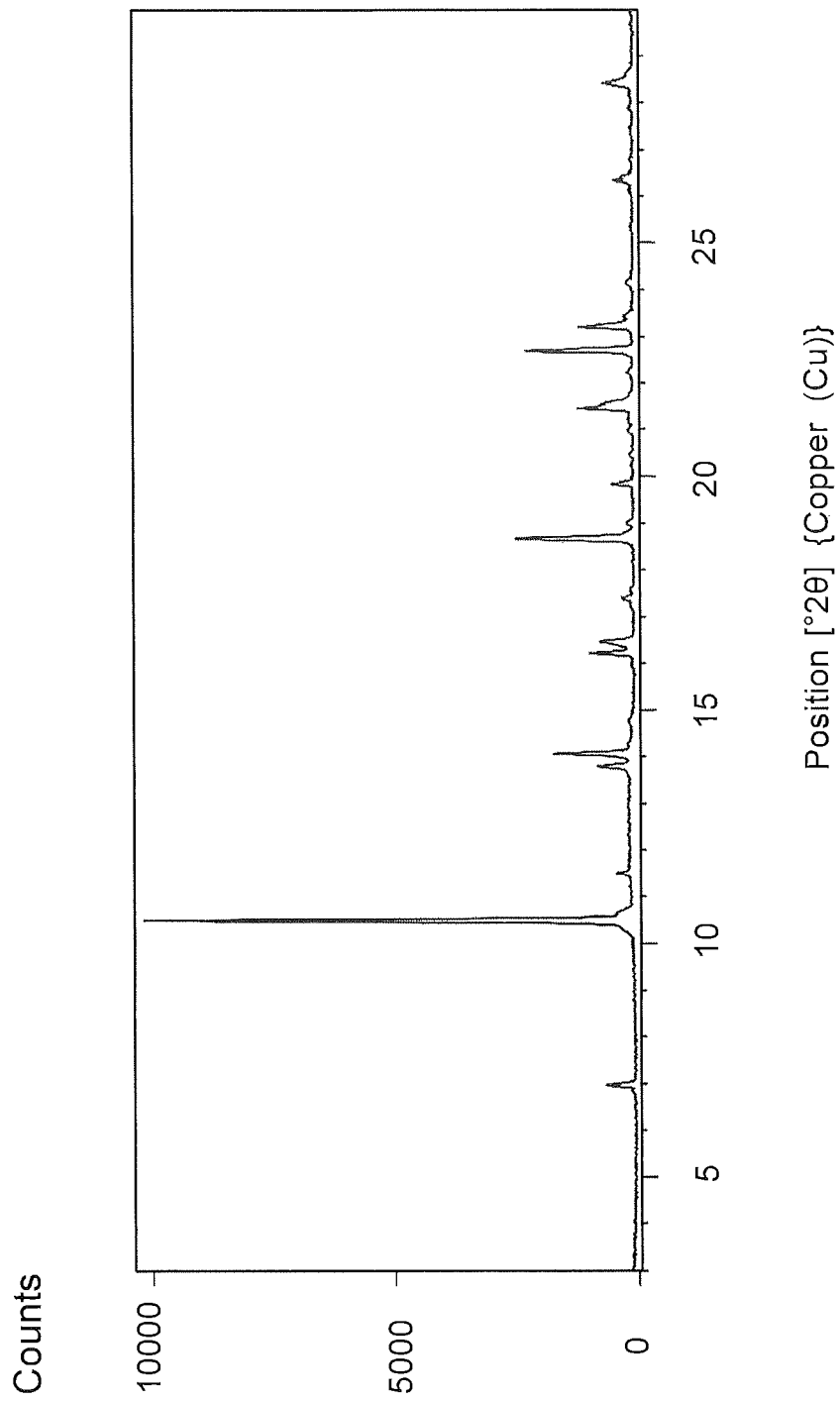
FIG. 7 is an X-ray powder diffraction pattern for crystalline 1-benzyl-8-methyl-1,4,8-triazaspiro-[4.5]-decan-2-one monohydrochloride, Crystalline Form 2.

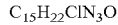 Chemical Formula:

FIG. 7 is an X-ray powder diffraction (XRPD) pattern for crystalline 1-benzyl-8-methyl-1,4,8-triazaspiro-[4.5]-decan-2-one monohydrochloride, Crystalline Form 2 obtained as described for FIG. 4, except that the peaks presented were selected to have at least 5% intensity of the most intense peak and to be lower than 2θ=30°.

Table 13 lists the positions, °2θ±0.2° 2θ, d-spacing and relative intensity of peaks identified in the experimental XRPD pattern of FIG. 7. The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 7.

Table 14 lists peaks identified in the experimental XRPD pattern of FIG. 7 that do not overlap with peaks in the XRPD diffraction patterns of other polymorphs and that represent preferred peaks to identify the crystalline form.

TABLE 13

| Position [°2θ] | d-spacing Å | Intensity in % |
|---|---|---|
| 7.0 | 12.67 | 5.9 |
| 10.5 | 8.43 | 100.0 |
| 13.8 | 6.42 | 7.5 |
| 14.1 | 6.30 | 16.4 |
| 16.2 | 5.47 | 8.7 |
| 16.5 | 5.38 | 6.7 |
| 18.7 | 4.75 | 24.0 |
| 21.5 | 4.14 | 11.2 |
| 22.7 | 3.92 | 21.6 |
| 23.2 | 3.83 | 11.0 |
| 28.4 | 3.14 | 5.4 |

Peaks presented were selected to be lower than 2 theta = 30°, and % intensity greater than 5%.

TABLE 14

| Position [°2θ] | d-spacing Å | intensity in % |
|---|---|---|
| 10.5 | 8.43 | 100.0 |
| 13.8 | 6.42 | 7.5 |
| 22.7 | 3.92 | 21.5 |

Peaks presented were selected to be lower than 2 theta = 30°, and % intensity greater than 5%.

C0105 Mono-HCl Salt: Form 3

Figure 8:
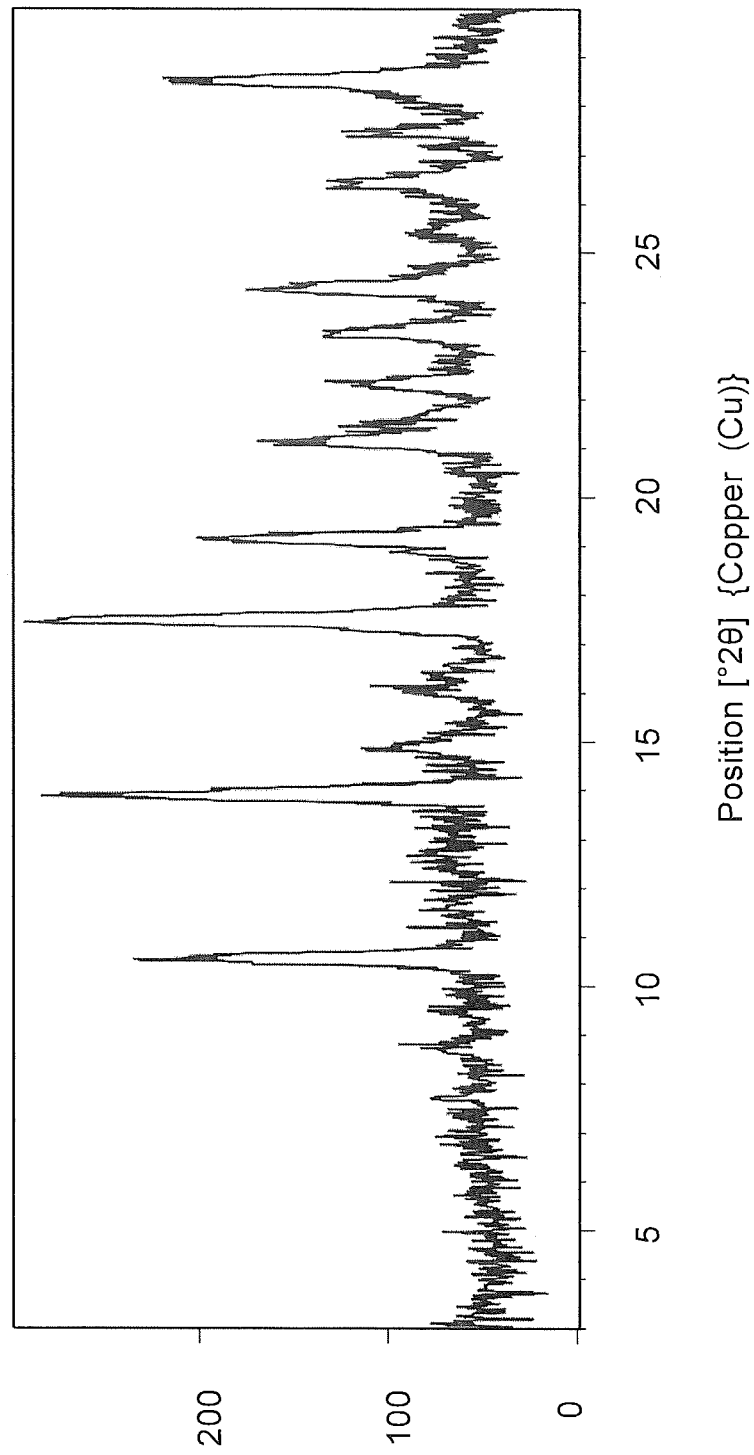
FIG. 8 is an X-ray powder diffraction (XRPD) pattern for crystalline 1-benzyl-8-methyl-1,4,8-triazaspiro-[4.5]-decan-2-one monohydrochloride, Crystalline Form 3.

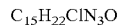 Chemical Formula:

FIG. 8 is an X-ray powder diffraction (XRPD) pattern for action pattern for crystalline 1-benzyl-8-methyl-1,4,8-triazaspiro-[4.5]-decan-2-one monohydrochloride, Crystalline Form 3 obtained as described for FIG. 4, except that the peaks presented were selected to have at least 5% intensity of the most intense peak and to be lower than 2θ=30°. Table 15 lists the positions, ° 2θ±0.2° 2θ, d-spacing and relative intensity of peaks identified in the experimental XRPD pattern of FIG. 8.

The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 8.

Table 16 lists peaks identified in the experimental XRPD pattern of FIG. 8 that do not overlap with peaks in the XRPD diffraction patterns of other polymorphs and that represent preferred peaks to identify the crystalline form. Table 17 lists a characteristic peak identified in the experimental XRPD pattern of FIG. 8 that can slightly overlap with peaks in the XRPD diffraction patterns of other polymorphs.

TABLE 15

| Position [°2θ] | d-spacing [Å] | Intensity in % |
|---|---|---|
| 10.3 | 8.57 | 30.2 |
| 13.6 | 6.49 | 85.1 |
| 14.6 | 6.06 | 23.4 |
| 15.8 | 5.62 | 17.9 |
| 16.3 | 5.44 | 8.1 |
| 17.2 | 5.15 | 100.0 |
| 18.9 | 4.71 | 76.2 |
| 20.8 | 4.27 | 53.4 |
| 21.3 | 4.17 | 25.2 |
| 22.0 | 4.03 | 39.9 |
| 23.0 | 3.86 | 55.7 |
| 24.0 | 3.71 | 71.5 |
| 25.2 | 3.54 | 11.7 |
| 26.1 | 3.41 | 31.0 |

TABLE 15-continued

| Position [°2θ] | d-spacing [Å] | Intensity in % |
|---|---|---|
| 27.2 | 3.28 | 27.1 |
| 27.7 | 3.22 | 14.6 |
| 28.2 | 3.16 | 83.8 |

Peaks presented were selected to be lower than 2 theta = 30°, and % intensity greater than 5%.

TABLE 16

| Position [°2θ] | d-spacing [Å] | Intensity in % |
|---|---|---|
| 13.6 | 6.49 | 85.1 |
| 15.8 | 5.62 | 17.9 |
| 20.8 | 4.27 | 53.4 |
| 22.0 | 4.03 | 39.9 |
| 27.2 | 3.28 | 27.1 |

Peaks presented were selected to be lower than 2 theta = 30°, and % intensity greater than 5%.

TABLE 17

| Position [°2θ] | d-spacing [Å] | Intensity in % |
|---|---|---|
| 10.3 | 8.57 | 30.2 |
| 23.1 | 3.86 | 55.7 |
| 24.0 | 3.71 | 71.5 |

Peaks presented were selected to be lower than 2 theta = 30°, and % intensity greater than 5%.

C0105 Mono-HCl Salt: Form 4

Figure 9:
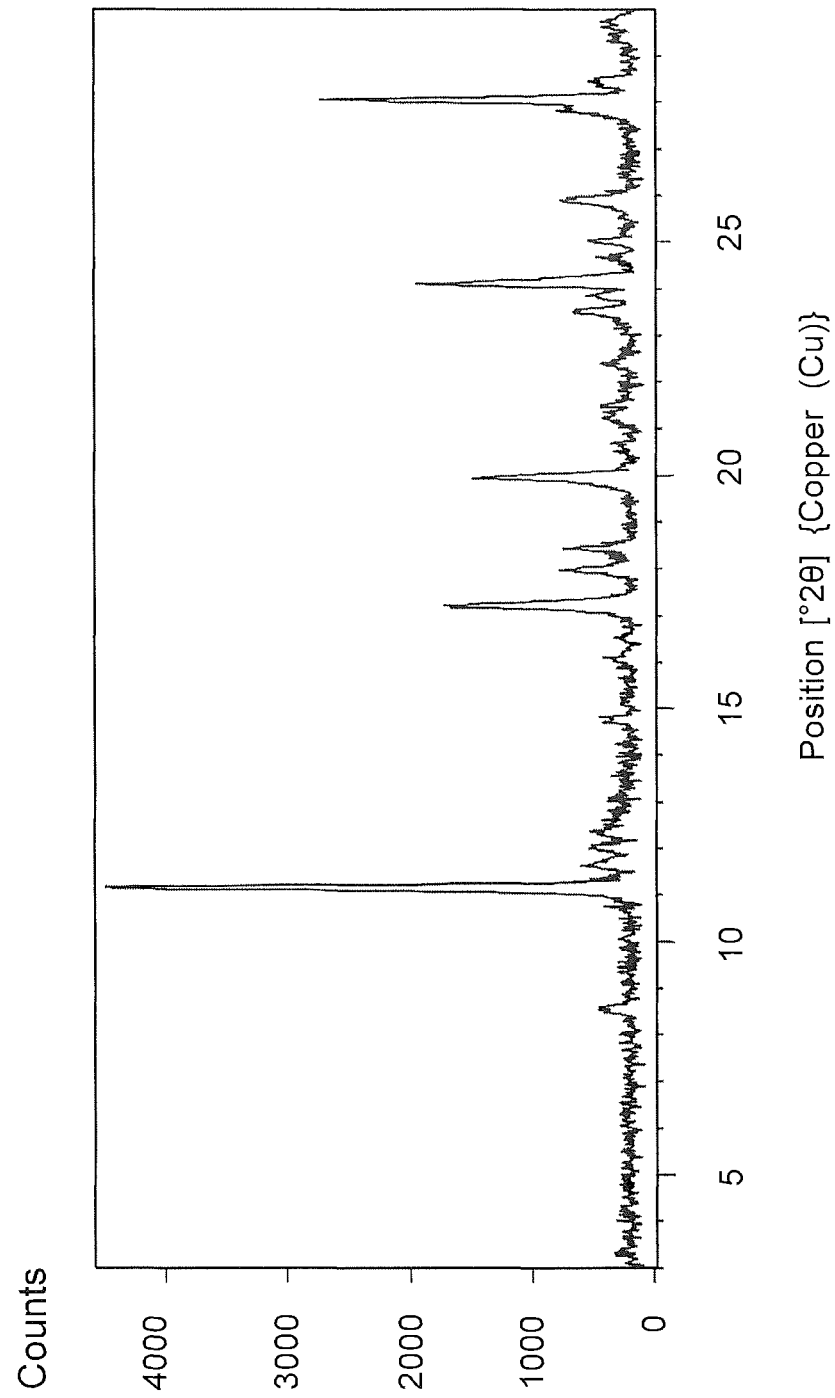
FIG. 9 is an X-ray powder diffraction (XRPD) pattern for crystalline 1-benzyl-8-methyl-1,4,8-triazaspiro-[4.5]-decan-2-one monohydrochloride, Crystalline Form 4.

$C_{15}H_{22}ClN_3O$      Chemical Formula:

FIG. 9 is an X-ray powder diffraction (XRPD) pattern for crystalline 1-benzyl-8-methyl-1,4,8-triazaspiro-[4.5]-decan-2-one monohydrochloride, Crystalline Form 4 obtained as described for FIG. 4, except that the peaks presented were selected to have at least 5% intensity of the most intense peak and to be lower than 2θ=30°. Table 18 lists the positions, ° 2θ±0.2° 2θ, d-spacing and relative intensity of peaks identified in the experimental XRPD pattern of FIG. 9. The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 9.

Table 19 lists peaks identified in the experimental XRPD pattern of FIG. 9 that do not overlap with peaks in the XRPD diffraction patterns of other polymorphs and that represent preferred peaks to identify the crystalline form. Table 20 lists a characteristic peak identified in the experimental XRPD pattern of FIG. 9 that can slightly overlap with peaks in the XRPD diffraction patterns of other polymorphs.

TABLE 18

| Position [°2θ] | d-spacing Å | intensity in % |
|---|---|---|
| 8.5 | 10.35 | 5.2 |
| 11.2 | 7.92 | 100.0 |
| 11.6 | 7.59 | 5.4 |
| 17.2 | 5.16 | 35.5 |
| 18.0 | 4.94 | 14.4 |
| 18.4 | 4.81 | 13.7 |
| 20.0 | 4.45 | 31.9 |
| 21.2 | 4.18 | 5.4 |

TABLE 18-continued

| Position [°2θ] | d-spacing Å | intensity in % |
|---|---|---|
| 21.5 | 4.13 | 5.6 |
| 22.4 | 3.97 | 5.5 |
| 23.6 | 3.78 | 13.1 |
| 23.9 | 3.72 | 9.0 |
| 24.1 | 3.69 | 43.6 |
| 24.7 | 3.61 | 5.9 |
| 25.0 | 3.56 | 9.1 |
| 25.9 | 3.44 | 13.4 |
| 27.8 | 3.21 | 11.0 |
| 28.0 | 3.18 | 48.6 |
| 28.0 | 3.13 | 6.6 |

Peaks presented were selected to be lower than 2 theta = 30°, and % intensity greater than 5%.

TABLE 19

| Position [°2θ] | d-spacing Å | intensity in % |
|---|---|---|
| 11.2 | 7.92 | 100.0 |
| 18.0 | 4.94 | 14.4 |
| 20.0 | 4.45 | 31.9 |

Peaks presented were selected to be lower than 2 theta = 30°, and % intensity greater than 5%.

TABLE 20

| Position [°2θ] | d-spacing Å | intensity in % |
|---|---|---|
| 23.6 | 3.78 | 13.1 |
| 25.9 | 3.44 | 13.4 |
| 28.0 | 3.18 | 48.6 |

Peaks presented were selected to be lower than 2 theta = 30°, and % intensity greater than 5%.

C0105 Free Base: Form 1

Figure 10:
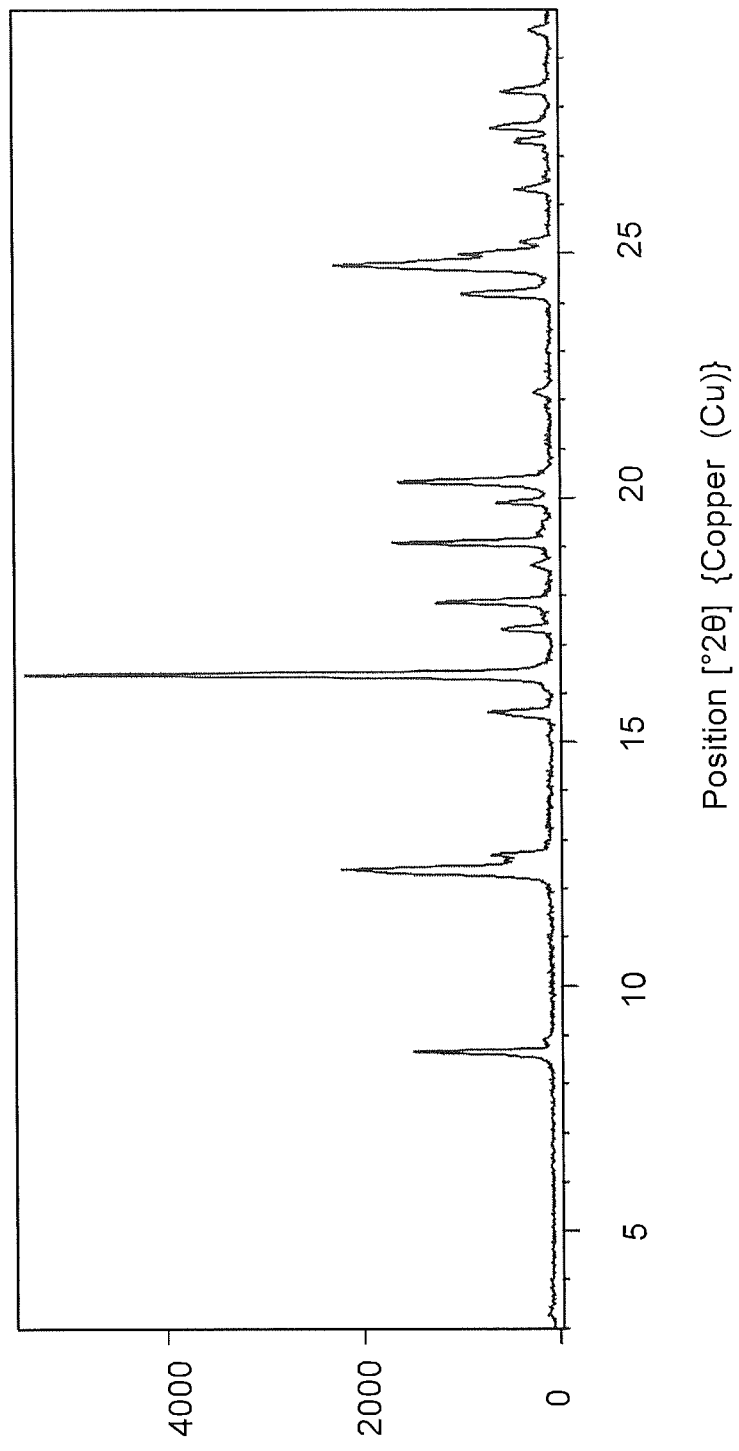
FIG. 10 is an X-ray powder diffraction (XRPD) pattern for crystalline 1-benzyl-8-methyl-1,4,8-triazaspiro-[4.5]-decan-2-one free base, Crystalline Form 1.

$C_{15}H_{21}N_3O$      Chemical Formula:

FIG. 10 is an X-ray powder diffraction (XRPD) pattern for crystalline 1-benzyl-8-methyl-1,4,8-triazaspiro-[4.5]-decan-2-one free base, Crystalline Form 1 obtained as described for FIG. 4, except that the peaks presented were selected to have at least 5% intensity of the most intense peak and to be lower than 2θ=30°.

Table 21 lists the positions, °2θ±0.2° 2θ, d-spacing and relative intensity of peaks identified in the experimental XRPD pattern of FIG. 10. The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 10.

Table 22 lists peaks identified in the experimental XRPD pattern of FIG. 10 that do not overlap with peaks in the XRPD diffraction patterns of other polymorphs and that represent preferred peaks to identify the crystalline form. Table 23 lists a characteristic peak identified in the experimental XRPD pattern of FIG. 10 that can slightly overlap with peaks in the XRPD diffraction patterns of other polymorphs.

TABLE 21

| Position [°2θ] | d-spacing Å | intensity in % |
|---|---|---|
| 8.7 | 10.21 | 25.4 |
| 12.4 | 7.14 | 38.8 |
| 12.7 | 6.97 | 11.9 |
| 15.6 | 5.68 | 12.5 |
| 16.4 | 5.42 | 100.0 |
| 17.3 | 5.13 | 10.6 |
| 17.9 | 4.96 | 22.7 |
| 18.6 | 4.77 | 5.6 |
| 19.1 | 4.65 | 30.9 |
| 19.9 | 4.46 | 11.3 |
| 20.3 | 4.37 | 29.2 |
| 24.1 | 3.69 | 15.0 |
| 24.8 | 3.59 | 39.4 |
| 25.0 | 3.56 | 14.1 |
| 25.2 | 3.53 | 5.6 |
| 26.3 | 3.39 | 6.4 |
| 27.3 | 3.27 | 6.5 |
| 27.6 | 3.24 | 10.8 |
| 28.3 | 3.15 | 8.8 |

Peaks presented were selected to be lower than 2 theta = 30°, and % intensity greater than 5%.

TABLE 22

| Position [°2θ] | d-spacing Å | intensity in % |
|---|---|---|
| 24.1 | 3.69 | 15.0 |
| 26.3 | 3.39 | 6.4 |
| 27.3 | 3.27 | 6.5 |

Peaks presented were selected to be lower than 2 theta = 30°, and % intensity greater than 5%.

TABLE 23

| Position [°2θ] | d-spacing Å | intensity in % |
|---|---|---|
| 8.7 | 10.21 | 25.4 |
| 12.7 | 6.97 | 11.9 |
| 16.4 | 5.41 | 100.0 |
| 24.8 | 3.59 | 39.4 |
| 27.6 | 3.24 | 10.8 |

Peaks presented were selected to be lower than 2 theta = 30°, and % intensity greater than 5%.

C0105 Free Base: Form 2

Figure 11:
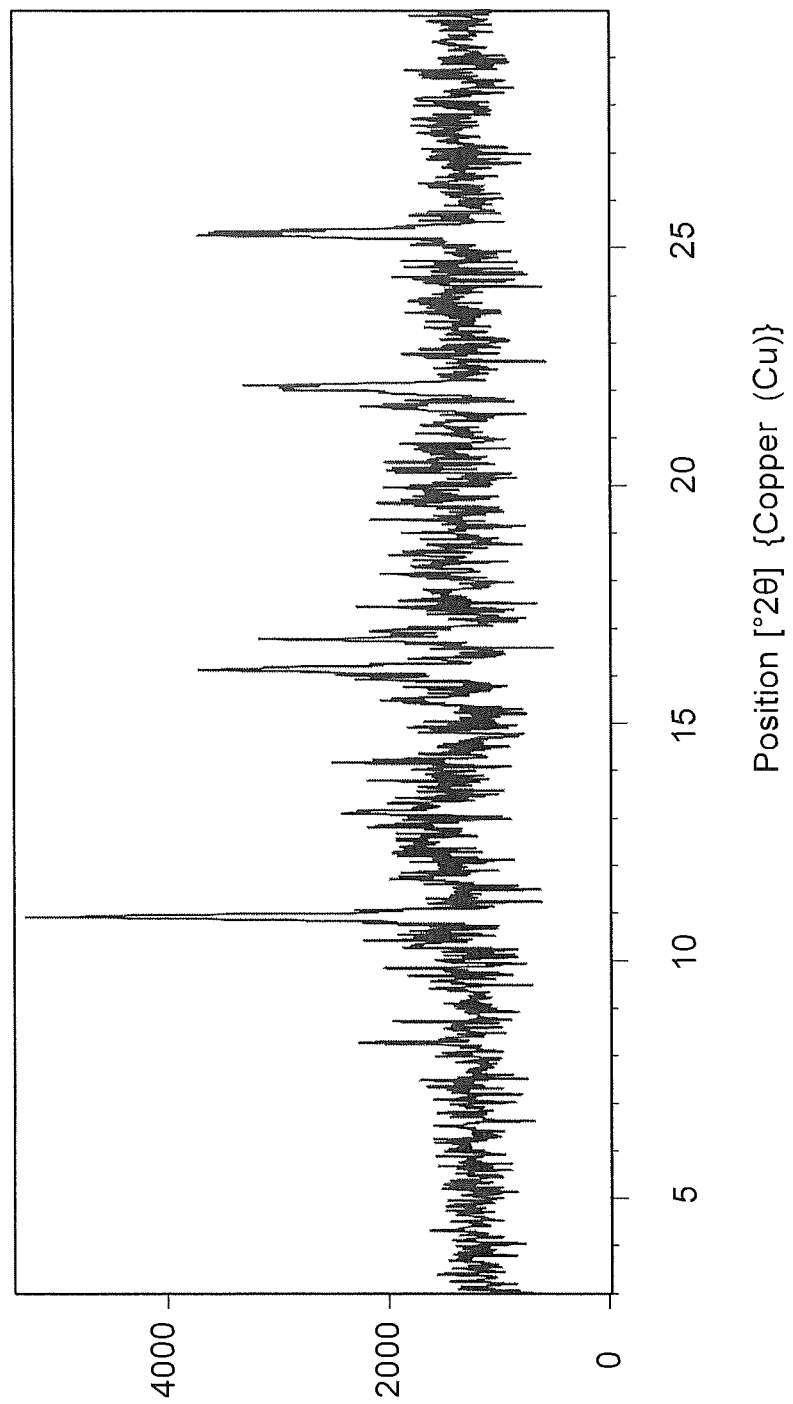
FIG. 11 is an X-ray powder diffraction (XRPD) pattern for crystalline 1-benzyl-8-methyl-1,4,8-triazaspiro-[4.5]-decan-2-one free base, Crystalline Form 2.

$C_{15}H_{21}N_3O$  Chemical Formula:

FIG. 11 is an X-ray powder diffraction (XRPD) pattern for crystalline 1-benzyl-8-methyl-1,4,8-triazaspiro-[4.5]-decan-2-one free base, Crystalline Form 2 obtained as described for FIG. 4, except that the peaks presented were selected to have at least 5% intensity of the most intense peak and to be lower than 2θ=30°. Table 24 lists the positions, °2θ±0.2° 2θ, d-spacing and relative intensity of peaks identified in the experimental XRPD pattern of FIG. 11.

The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 11. Table 25 lists peaks identified in the experimental XRPD pattern of FIG. 11 that do not overlap with peaks in the XRPD diffraction patterns of other polymorphs and that represent preferred peaks to identify the crystalline form.

Table 26 lists a characteristic peak identified in the experimental XRPD pattern of FIG. 11 that can slightly overlap with peaks in the XRPD diffraction patterns of other polymorphs.

TABLE 24

| Position [°2θ] | d-spacing [Å] | intensity in % |
|---|---|---|
| 8.3 | 10.66 | 9.7 |
| 10.9 | 8.09 | 100.0 |
| 13.1 | 6.74 | 13.8 |
| 15.5 | 5.71 | 12.4 |
| 16.2 | 5.48 | 60.8 |
| 16.8 | 5.27 | 20.8 |
| 21.7 | 4.10 | 13.2 |
| 22.1 | 4.02 | 47.9 |
| 25.3 | 3.52 | 68.4 |

Peaks presented were selected to be lower than 2 theta = 30°, and % intensity greater than 5%.

TABLE 25

| Position [°2θ] | d-spacing Å | intensity in % |
|---|---|---|
| 13.1 | 6.74 | 13.8 |
| 16.8 | 5.27 | 20.8 |

Peaks presented were selected to be lower than 2 theta = 30°, and % intensity greater than 5%.

TABLE 26

| Position [°2θ] | d-spacing Å | intensity in % |
|---|---|---|
| 10.9 | 8.09 | 100.0 |
| 15.5 | 5.71 | 12.4 |
| 25.3 | 3.52 | 68.4 |

Peaks presented were selected to be lower than 2 theta = 30°, and % intensity greater than 5%.

C0105 Free Base: Form 3

Figure 12:
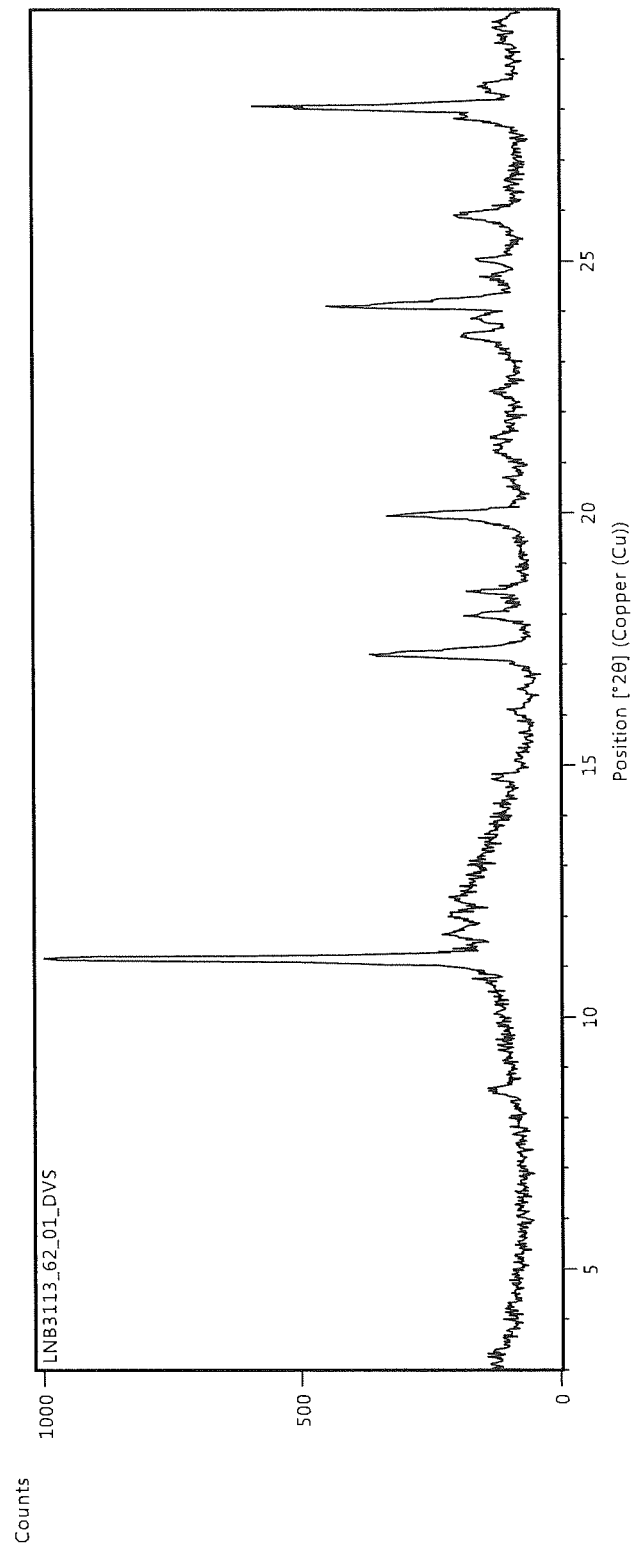
FIG. 12 is an X-ray powder diffraction (XRPD) pattern for crystalline 1-benzyl-8-methyl-1,4,8-triazaspiro-[4.5]-decan-2-one free base, Crystalline Form 3.

$C_{15}H_{21}N_3O$  Chemical Formula:

FIG. 12 is an X-ray powder diffraction (XRPD) pattern for crystalline 1-benzyl-8-methyl-1,4,8-triazaspiro-[4.5]-decan-2-one free base, Crystalline Form 3 obtained as described for FIG. 4, except that the peaks presented were selected to have at least 5% intensity of the most intense peak and to be lower than 2θ=30°. Table 27 lists the positions, ° 2θ±0.2° 2θ, d-spacing and relative intensity of peaks identified in the experimental XRPD pattern of FIG. 12.

The entire list of peaks, or a subset thereof, can be sufficient to characterize the crystalline form, as well as by an XRPD pattern substantially similar (that is, identifiable by one of ordinary skill using a characterization method, such as this one, within experimental variations) to FIG. 12.

Table 28 lists peaks identified in the experimental XRPD pattern of FIG. 12 that do not overlap with peaks in the XRPD diffraction patterns of other polymorphs and that represent preferred peaks to identify the crystalline form. Table 29 lists a characteristic peak identified in the experimental XRPD pattern of FIG. 12 that can slightly overlap with peaks in the XRPD diffraction patterns of other polymorphs.

TABLE 27

| Position [°2θ] | d-spacing Å | intensity in % |
|---|---|---|
| 10.1 | 8.78 | 100.0 |
| 11.0 | 8.03 | 5.4 |
| 12.2 | 7.27 | 16.7 |

TABLE 27-continued

| Position [°2θ] | d-spacing Å | intensity in % |
|---|---|---|
| 14.3 | 6.19 | 61.7 |
| 16.0 | 5.53 | 13.6 |
| 16.2 | 5.47 | 40.4 |
| 17.8 | 4.99 | 63.7 |
| 18.5 | 4.79 | 66.5 |
| 18.7 | 4.75 | 55.5 |
| 19.3 | 4.59 | 24.5 |
| 19.9 | 4.46 | 8.9 |
| 20.2 | 4.40 | 27.6 |
| 21.4 | 4.15 | 14.8 |
| 21.6 | 4.12 | 14.6 |
| 22.3 | 3.98 | 20.4 |
| 22.8 | 3.90 | 14.4 |
| 27.8 | 3.21 | 5.8 |
| 28.1 | 3.18 | 9.2 |
| 28.2 | 3.16 | 10.7 |
| 29.8 | 2.99 | 5.5 |

Peaks presented were selected to be lower than 2 theta = 30°, and % intensity greater than 5%.

TABLE 28

| Position [°2θ] | d-spacing Å | intensity in % |
|---|---|---|
| 10.1 | 8.78 | 100.0 |
| 14.1 | 6.19 | 61.7 |
| 19.3 | 4.59 | 24.5 |

Peaks presented were selected to be lower than 2 theta = 30°, and % intensity greater than 5%.

TABLE 29

| Position [°2θ] | d-spacing Å | intensity in % |
|---|---|---|
| 20.2 | 4.40 | 27.6 |
| 28.1 | 3.18 | 9.2 |

Peaks presented were selected to be lower than 2 theta = 30°, and % intensity greater than 5%.

Pharmaceutical Compositions

A contemplated compound polymorph or solvatomorph can be provided for use by itself in salt or free base form. Regardless of whether in the form of a salt or not and a solvate or not, an effective amount of a contemplated solid polymorph is typically dissolved or dispersed in a physiologically tolerable carrier or diluent that forms a pharmaceutical composition of which the polymorph is an API, typically, the only API. Such a pharmaceutical composition is administered in vitro or in vivo to the CNS and/or other cells for the API to bind to FLNA and illustratively inhibit tau protein phosphorylation, inhibit the interaction of FLNA with α7nAChR and TLR4, as well as inhibit the interaction of $A\beta_{42}$ with α7nAChR, or to reduce one or both of pain and inflammation.

A contemplated polymorph can be used in the manufacture of a medicament (pharmaceutical composition) that is useful at least for inhibiting tau protein phosphorylation in mammalian cells and mammalian cell preparations. A contemplated solid polymorph compound can also be used in the manufacture of a medicament that is useful at least for inhibiting the interaction of FLNA with α7nAChR and TLR4, as well as of $A\beta_{42}$ with α7nAChR, or to reduce one or both of pain and inflammation in mammalian cells and mammalian cell preparations.

A contemplated pharmaceutical composition contains an effective amount of a contemplated solid API polymorph (free base polymorph or a mono- or dihydrochloride salt hydrate or other solvatomorph) as discussed previously dissolved or dispersed in a physiologically tolerable carrier or diluent. Such a composition can be administered to mammalian cells or a cell preparation in vitro as in a cell culture or protein binding study, or in vivo as in a living, host mammal in need.

A contemplated composition is typically administered a plurality of times over a period of days, weeks or months to a living recipient. More usually, a contemplated composition is administered once, twice or more times daily, with that administration being repeated. It is contemplated that once administration of a contemplated polymorph has begun, that polymorph is administered chronically, such as for the duration of the study being carried out or for a recipient's lifetime.

A contemplated free base polymorph can bind to FLNA at a 100 femtomolar concentration and effectively inhibit cytokine release from LPS-stimulated astrocytes in vitro. A contemplated polymorph mono- or dihydrochloride salt binds at about the same molar concentration as the free base, and at a proportional weight percentage based on the free base. A contemplated polymorph is more usually utilized at picomolar to micromolar amounts.

Thus, an effective amount of a contemplated polymorph present in a contemplated pharmaceutical composition is that which provides a concentration of about 100 femtomolar to about 10 micromolar to a host animal's blood stream or to an in vitro cell medium in practicing a contemplated method of the invention. A more usual amount is about picomolar to about micromolar. A still more usual amount is about picomolar to about nanomolar. A skilled worker can readily determine an appropriate dosage level of a contemplated compound to inhibit a desired amount of FLNA binding.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., Remington's Pharmaceutical Sciences, Mack Publishing Co., Easton, Pa., 1975 and Liberman, H. A. and Lachman, L., Eds., *Pharmaceutical Dosage Forms*, Marcel Decker, New York, N.Y., 1980.

For injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Where a solid polymorph API is desired to be in solution, the compound is typically supplied as a solid, preferably free of liquid, or in suspension in a non-solvent liquid to which a solvent such as aqueous normal saline is added to dissolve the solid API polymorph. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an API or sterile solution of the API in solvents comprising water, ethanol, or propylene glycol are examples of liquid compositions suitable for parenteral administration.

In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables. Dimethyl-acetamide, surfactants including ionic and non-ionic detergents, polyethylene glycols can be used. Mixtures of solvents and wetting agents such as those discussed above are also useful.

Sterile solutions can be prepared by dissolving a contemplated polymorph in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a contemplated compound is ordinarily combined with one or more excipients appropriate to the indicated route of administration. If administered per os, the compounds can be admixed with lactose, sucrose, starch powder, cellulose esters of $C_1$-$C_6$-alkanoic acids, cellulose $C_1$-$C_6$-alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets, capsules and pills can additionally be prepared with enteric coatings.

A mammal in need of treatment and to which a pharmaceutical composition containing a contemplated solid polymorph API or a solution containing a dissolved polymorph API is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like. Where in vitro mammalian cell contact is contemplated, a CNS tissue culture of cells from an illustrative mammal is often utilized, as is illustrated hereinafter.

Preferably, the pharmaceutical composition is in unit dosage form. In such form, the composition is divided into unit doses containing appropriate quantities of the active agent. The unit dosage form can be a packaged preparation, the package containing discrete quantities of the preparation, for example, in vials or ampules.

Analytical Procedures

Specific compounds were identified using standard chemical analyses such as elemental analysis (CHN; ASTM D5291), high resolution mass spectroscopy (MS), $^1$H-NMR, $^{13}$C-NMR and 2D-NMR spectroscopy, and infrared spectroscopy (IR) as carried out by third party vendors. Physical property assays were similarly carried out using techniques such as X-ray particle diffraction (XRPD) for polymorph determinations as discussed in detail herein, melting point by differential scanning calorimetry (DSC) and mass loss by thermos gravimetric analysis (TGA). Water content was determined by Karl Fisher analysis. High pressure liquid chromatography (HPLC) was used to assay compound purity.

Polymorph Preparation

Dihydrochloride Polymorph Form 1 Hydrate

Preparation 1

The synthesis of Compound C0105 (C0105M) was carried out in some instances as discussed in U.S. Pat. No. 8,653,068. An alternative synthesis was carried out using the reaction scheme shown and discussed below.

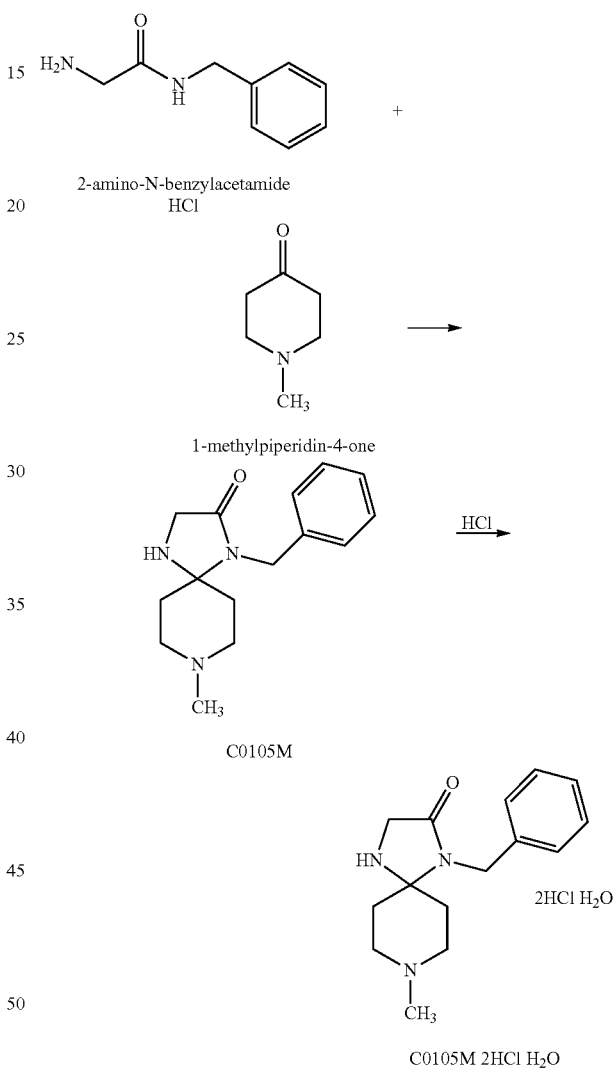

N-t-Boc glycine was amidified with benzylamine in dichloromethane in the presence of 1-ethyl-3-(3-dimethylaminopropyl)carbodiimide hydrochloride, triethylamine and ethyl cyano(hydroxyimino)acetate to form 2-amino-N-benzylacetamide. That product was then converted into its hydrochloride salt by treatment with HCl in 2-propanol (iso-propanol).

A flask was charged with 2-amino-N-benzylacetamide HCl salt and isopropanol (8 vol). To the suspension was added 1-methylpiperidin-4-one (1.10 eq) followed by a rinse with methanol (2 vol). The heterogenous mixture was stirred at reflux for 20 hours. HPLC analysis showed 94% conversion after 20 hours. The solution was cooled to 45-55° C.

and 30% HCl (aq., 1.5 eq) was added drop-wise resulting in precipitation. The resulting slurry was cooled to ambient temperature and filtered after 3 hours. The isolated solids were washed with MeOH (2×1 vol.) and the solids were air dried, resulting in a yield of 80% of the dihydrochloride hydrate of Polymorph Form 1, whose X-ray powder diffraction (XRPD) spectrum is shown in FIG. 1. Ethanol, ethyl acetate and tetrahydrofuran (THF) can also be used as solvent.

Conversion of Mono-HCl into Di-HCl Hydrate Salt

HCl mono-salt was mixed with 8 mL of 2-propanol and the resulting suspension was stirred at about 50° C. for about 1 hour at which time a solution of 37% HCl (1.6 mL, 2 equiv.) in 1.6 mL 2-propanol was added. The mixture was then cooled to ambient temperature initially and then, after equilibration, to about 2-3° C. An additional 5 mL of 2-propanol was added to the sample after cooling. The resulting white precipitate was filtered and washed with 2-propanol (2×7 mL aliquots). The isolated solid was dried under vacuum for about 24 hours at ambient temperature. Approximately 2 g of solid material of mono-hydrate Form 1 was recovered (yield: 66%). This polymorph can also be formed using ethanol, ethyl acetate or tetrahydrofuran as the solvent in place of 2-propanol.

Preparation 2

Purified water (2.4 kg, 3.0 vol.) was charged to form a 2-phase mixture that was stirred for 9 minutes. The measured pH value of the lower aqueous layer (target pH ≥7) was pH=8. Phase separation occurred under static conditions and the aqueous layer was removed and discarded.

Aqueous hydrochloric acid (30%; 0.032 kg, 0.03 vol.) in purified water (2.4 kg, 3.0 vol.) was charged and the resulting 2-phase mixture was stirred for 8 minutes to form the intermediate salt product. The measured pH value of the lower aqueous layer (target pH ≤2) was pH=1. Phase separation occurred under static conditions, the aqueous layer was removed and discarded. HPLC analysis showed 97% purity of the isolated intermediate N-Boc-2-amino-N-benzylacetamide.

While stirring, the reaction mixture was distilled at 40°±5° C. under reduced pressure to remove approximately 6 relative volumes of volatiles. Isopropanol (2.5 kg, 4 vol.) was charged to the reactor. The reaction mixture was distilled at 40±5° C. to remove approximately 4 relative volumes of volatiles. The reaction mixture was cooled to 20±5° C. and held.

Cleavage of the Boc Protective Group

Isopropanol (IPA) was charged into (3.2 kg, 5 vol.) an empty reactor. While being stirred and cooled (15°-35° C.), hydrogen chloride gas was fed under pressure into the reactor until approximately 5 equivalents were absorbed into the isopropanol.

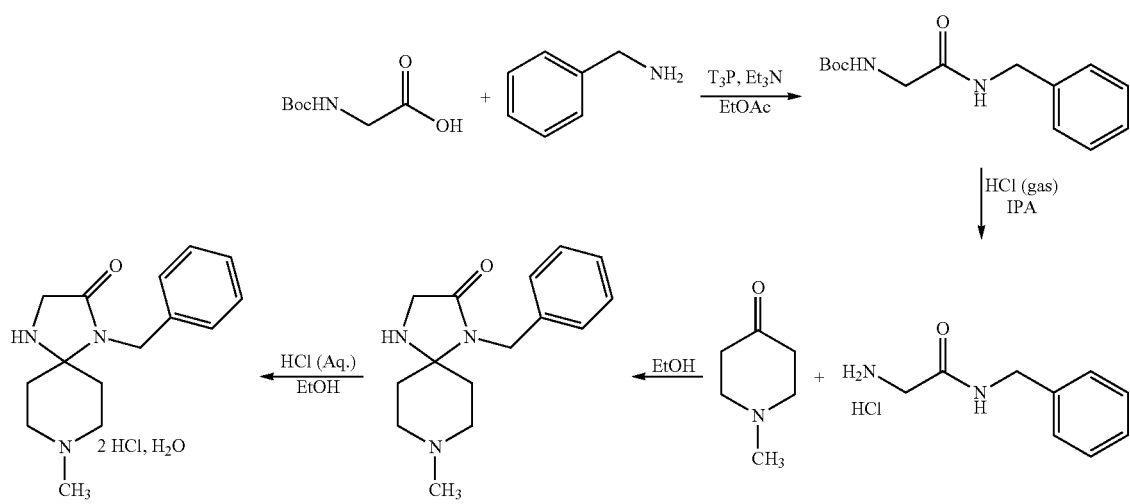

Amide Coupling of Boc Protected Glycine and Benzylamine

N-t-boc-glycine (0.808 kg) and ethyl acetate (EtOAc, 3.615 kg, 5.0 vol.) were charged into an nitrogen-purged reactor and stirred until a clear solution was obtained. The solution was chilled to 0-5° C. and benzylamine (0.534 kg, 1.10 equiv.) was dosed into the reactor while maintaining the chilled temperature. The dosing bulb was rinsed with EtOAc (0.50 vol.) and the resulting EtOAc composition was added.

Triethylamine (Et₃N, 2.2 equiv., Et₃N) followed by an EtOAc (0.50 vol.) rinsing was charged to the reactor. Propanephosphonic anhydride (T₃P) in 50% in EtOAc (3.493 kg, 1.20 equiv.) and a rinsing of EtOAc (0.50 vol.) was dosed into the reactor while maintaining the temperature at ≤25° C. The reaction mixture was stirred for 20 hours while the temperature was maintained at 20±5° C. HPLC analysis showed 91% conversion of benylamine.

Excess hydrogen chloride gas pressure in the reactor was vented. The above-prepared intermediate reaction mixture was dosed into the reactor with stirring and temperature control at 20°±5° C. The dosing bulb was rinsed with isopropanol (0.329 kg, 0.50 vol.), and the isopropanol composition was added to the reaction mixture. The reaction mixture temperature was controlled to 20±5° C. and stirred for 20 hours. HPLC analysis showed 99.4% conversion to 2-amino-N-benzylacetamide mono-HCl.

The product slurry was filtered to collect the solid intermediate product (2-amino-N-benzylacetamide mono-HCl). The filter cake was washed twice with isopropanol; wash 1 (0.633 kg, 1 vol.), wash 2 (0.328 kg, 0.5 vol.), and a third time with methyl tert-butylether (MTBE); wash 3 (0.641 kg, 1 vol.), and dried under reduced pressure at 20°±5° C. for 18 hours, which yielded 0.760 kg of the dried mono-HCl intermediate product. HPLC analysis showed 100.0% purity of the mono-HCl product. The structure was confirmed by $^1$H-NMR and the dried intermediate product held 0.23 wt-% volatiles from a loss on drying test.

Cyclization of 2-amino-N-benzylacetamide mono-HCl with 1-methylpiperidin-4-one

2-Amino-N-benzylacetamide mono-HCl (0.5 kg, 1 equiv.) and absolute ethanol (3.26 kg, 8.0 vol., EtOH) were charged to a nitrogen-purged reactor and vigorously stirred. 1-Methylpiperidin-4-one (0.310 kg, 1.1 equiv.) was dosed into the reactor and rinsed through with absolute ethanol (0.795 kg, 2 vols.). The reactor temperature was raised and held at 65°±5° C., and the reaction occurred over 18 hours. HPLC analysis showed 91% conversion to the cyclization product, 1-benzyl-8-methyl-1,4,8-triazaspiro-[4.5]-decan-2-one. The intermediate product slurry was cooled to 20°±5° C. and then filtered into a holding vessel, followed by addition of an absolute ethanol rinse (0.207 kg, 0.50 vol.) to provide a sol.

Conversion of the Cyclized Product to the 2HCl.H$_2$O Polymorph Form 1

The 1-benzyl-8-methyl-1,4,8-triazaspiro-[4.5]-decan-2-one sol and an absolute ethanol rinse (0.201 kg, 0.50 vol.) were charged to a reactor and stirred. The temperature was increased and maintained at 50±5° C. while aqueous hydrochloric acid 30% (0.457 kg, 1.5 equiv.) was slowly dosed into the reactor over 31 minutes followed by a rinse of absolute ethanol (0.206 kg, 0.5 vol.).

The reaction mixture was slowly cooled to 20°±5° C. over a two hour time period and stirred for an additional 4 hours while held at temperature. The temperature was cooled further to −15±5° C. over 2 hours and the reaction mixture stirred for an additional 11 hours while held at temperature. The resulting slurried product, 1-benzyl-8-methyl-1,4,8-triazaspiro-[4.5]-decan-2-one di-HCl H$_2$O, was separated by filtration. The filtered solids were washed at 15±5° C. with three rinses of absolute ethanol (about 2 vol. each) and then twice slurried in EtOAc (about 2 vol. each) and filtered. The final product was harvested after being dried at 20±5° C. for 23 hours.

HPLC analysis showed the final product purity at 100.0%. The structure was confirmed by $^1$H-NMR, $^{13}$C-NMR and 2D-NMR. The monohydrate product had 5.5 wt-% water content as determined by Karl Fischer titration. Polymorph Form 1 of the crystalline monohydrate product was confirmed by X-Ray Powder Diffraction (XRPD) by comparison with FIG. 1.

Dihydrochloride Polymorph Form 2 Mono-Hydrate

Approximately 9.6 g of Compound C0105 free base was mixed with 30 mL of 2-propanol. The resulting suspension was stirred at 50° C. for about 1 hour, followed by drop-wise addition of an aqueous solution of 37% HCl (9.3 mL, 3 equivalents) in 10 mL of 2-propanol. A white suspension was obtained that was stirred at 50° C. for about 1 hour, then at ambient room temperature for 1 hour, and finally at about 2° C. for 1 hour. The solid material recovered was filtered in vacuo and suspended in a mixture of acetone/water (20% water, 8 mL). The obtained slurry was temperature cycled between ambient and 40° C., in 4 hour cycles. The resulting solids were filtered and XRPD analysis after drying indicated a new polymorphic form labeled Form 2 dihydrochloride hydrate, whose XRPD spectrum is shown in FIG. 2.

Dihydrochloride Polymorph Form 3 DMA-Solvate

Approximately 25 mg of HCl di-salt (from conversion of HCl mono-salt to di-salt scale-up batch) was placed in a vial and 0.1 mL aliquots of dimethylacetamide added. Between each addition, the mixture was checked for dissolution and if no dissolution was apparent, the mixture was heated to about 50° C. and checked again. This procedure was continued until 2 mL of solvent had been added (dissolution did not occur).

The slurry was then temperature cycled between ambient temperature (about 22° C.) and 40° C. in 4 hour cycles for about 3 or 4 days (the cooling/heating rate after the 4 hour periods was about 1° C./minute). The slurry was cooled, filtered and the recovered solids were permitted to dry at ambient conditions prior to analysis. The XRPD spectrum is shown in FIG. 3.

Dihydrochloride Polymorph Form 4—Amorphous

About 25 mg of the di-HCl salt was slurried in 300-1000 μL of either heptane or toluene. The mixture was then temperature cycled (between 40° C. and RT). The resulting solids were filtered, and dried in vacuo. Analysis of the solids showed a unique XRPD spectral pattern labeled as Form 4 that contained no peaks as is seen in FIG. 4.

Dihydrochloride Polymorph Form 5 Mono-Hydrate

Approximately 20 mL of methanol was added to about 450 mg of the Di-HCl salt hydrate (Form 1). The suspension obtained was stirred at 50° C. for approximately 3 hours and the resulting solution was filtered at ambient temperature. The gel/solid mixture that was isolated, was dried in vacuo and mixed with about 0.1 mL of methanol. The resulting slurry was temperature cycled between ambient temperature and 40° C. in 4 hour cycles. The resulting solids were then filtered, and dried in vacuo. XRPD spectral analysis from the spectrum of FIG. 5 showed a new polymorphic form labeled Form 5 mono-hydrate.

Mono-HCl Salt Form 1

Approximately 3.5 g of Compound C0105 free base was dissolved in about 1 mL of 2-propanol at 40° C. and a solution of 1 equivalent of 37% HCl (1.128 mL) in 1.9 mL of 2-propanol was added to the mixture drop-wise under stirring at 40° C. The resulting mixture was cooled from 40° C. to 5° C. at a rate of about 1° C./minute. A suspension was obtained and stirred at ambient room temperature for a further 3 hours. The resulting white solid was filtered and dried at ambient conditions prior analysis. About 2.5 g of material was recovered of this new polymorphic form labeled Form 1. Another 0.2 g of solid was obtained from the mother liquors of this preparation by stirring for about 24 hours at 5° C., providing a total yield of 34%. The XRPD spectrum for this solid polymorphic compound is shown in FIG. 6.

Mono-HCl Salt Form 2

Approximately, 500 mg of C0105M free base was dissolved in 6 mL of 2-propanol and mixed with 1 equivalent of HCl (37%), dissolved in 2 mL of 2-propanol. The resulting solution was temperature cycled (between 40° C. and RT in 4 hour cycles) for 3 days. The XRPD spectrum of this solid polymorph is shown in FIG. 7.

Mono-HCl Salt Form 3

Prepared as Form 2, above, but the solid was dried under vacuum. The XRPD spectrum of this solid polymorph is shown in FIG. 8.

Mono-HCl Salt Form 4

The mother liquor and solid material recovered from the preparation of Form 2, above, were mixed together and seeded with about 10 mg of the HCl salt obtained from about 500 mg of C0105M free base dissolved in 6 mL of 2-propanol and mixed with 1 equivalent of HCl (37%), dissolved in 2 mL of 2-propanol. The resulting solution was temperature cycled (between 40° C. and RT in 4 hour cycles) for 3 days. The solid obtained from temperature cycling was dried under vacuum. The thereafter-obtained slurry was then temperature cycled between 40° C. and 20° C. for 24 hours and analyzed by DVS between 0 to 90% RH in 10% increments and 90 to 0% RH. The XRPD spectrum of this solid polymorph is shown in FIG. 9.

Free Base Form 1

The free base material utilized to prepare free base crystal Forms 1, 2 and 3 was received as a yellow gum-like solid that appeared to be amorphous. This material was prepared as discussed above under the heading "Preparation 2", and stopping prior to the final addition of hydrochloric acid in the last step shown.

Approximately 500 mg of that free base material was slurried in 0.5 mL of ethyl acetate and the resulting mixture was temperature cycled (between 40° C. and RT in 4 hour cycles) for 3 days. The crystal polymorph precipitated out on cooling, was recovered and is referred to herein as free base Form 1. The XRPD spectrum of this solid polymorph is shown in FIG. 10.

Free Base Form 2

2.4 Grams of C0105M free base gum was dissolved in 8.4 mL of methanol and 100 µL aliquots were transferred, separately, to 96 vials. The solvent was permitted to evaporate at ambient conditions to leave approximately 25 mg of C0105M in each of the 96 vials. 300 Microliters of ethyl acetate was added, which produced a gum. Temperature cycling between ambient temperature (about 22° C.) and 40° C. in 4 hour cycles for about 3 or 4 days (the cooling/heating rate after the 4 hour periods was about 1° C./minute) provided free base Form 2 crystals. The XRPD spectrum of this solid polymorph is shown in FIG. 11.

Free Base Form 3

Physically manipulating the surface of the as received free base gum with a spatula provided a white sticky powder. HPLC analysis of that powder indicated that it was 96.5% pure free base compound. Polarized light microscopy (PLM) analysis indicated that the material was birefringent under polarized light with a block-like morphology. XRPD analysis indicated that the material so obtained was crystalline. The XRPD spectrum of this polymorph is shown in FIG. 12.

Results

Procedures

X-Ray Powder Diffraction (XRPD)

XRPD analysis was carried out on a Siemens D5000, scanning the samples between 3 and 30° (or 50°, for input material) 2-theta (2θ). For samples <100 mg, 10-20 mg of material was gently compressed onto a glass disc inserted into an XRPD sample holder. For samples <20 mg, 5-10 mg of material was gently compressed onto a zero background disc inserted into an XRPD sample holder. For samples >100 mg, about 100 mg of material was gently compressed into a plastic XRPD sample holder to ensure a smooth sample surface, just above the level of the sample holder. The sample was then loaded into a Siemens D5000 or Panalytical X'Pert diffractometer running in reflection mode and analyzed, using the following conditions:

| Raw Data Origin | Siemens-binary V2 (.RAW) |
|---|---|
| Start Position [°2θ] | 3.0 |
| End Position [°2θ] | 30.0 (or 50.0) |
| Step Size [°2θ] | 0.020 |
| Scan Step Time [s] | 1 |
| Scan Type | Continuous |
| Offset [°2θ] | 0.0 |
| Divergence Slit Type | Fixed |
| Divergence Slit Size [mm] | 2.00 |
| Specimen Length [mm] | various |
| Receiving Slit Size [mm] | 0.2 |
| Measurement Temperature [° C.] | 20.0 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50 (nominal) |
| Generator Settings | 40 mA, 40 kV |
| Diffractometer Type | D5000 |
| Diffractometer Number | 0 |
| Goniometer Radius [mm] | 217.50 |
| Incident Beam Monochromator | No |
| Diffracted Beam Monochromator | (Graphite) |
| Spinning | No |

Further XRPD analysis was carried out on a Panalytical X'pert (PANalytical B.V., Westborough, Mass.) powder, scanning the samples between 3 and 35° 2θ. The material was gently ground and loaded onto a multi-well plate with Kapton® polyimide or Mylar® polyester film to support the sample. The multi-well plate was then loaded into a PANalytical diffractometer (Westborough, Mass.) running in transmission mode and analyzed, using the following experimental conditions.

| Raw Data Origin | XRD measurement (*.XRDML) |
|---|---|
| Scan Axis | Gonio |
| Start Position [°2θ] | 3.0066 |
| End Position [°2θ] | 34.9866 |
| Step Size [°2θ] | 0.0130 |
| Scan Step Time [s] | 18.8700 |
| Scan Type | Continuous |
| PSD Mode: | Scanning |
| PSD Length [°2θ] | 3.35 |
| Offset [°2θ] | 0.0 |
| Divergence Slit Type | Fixed |
| Divergence Slit Size [mm] | 1.0000 |
| Measurement Temperature [° C.] | 25.0 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50 |
| Generator Settings | 40 mA, 40 kV |
| Goniometer Radius [mm] | 240.00 |
| Dist. Focus Diverg. Slit [mm] | 91.00 |
| Incident Beam Monochromator | No |
| Spinning | No |

Still other XRPD analyses were carried out on the Bruker D2 Phaser with zero background discs inserted in XRPD sample holder. The following method was used:

| Start Position [°2θ] | 5.0000 |
|---|---|
| End Position [°2θ] | 30.0000 |
| Step Size[°2θ] | 0.04° °2θ |
| Scan Step Time[s] | 0.25 |
| Generator Settings | 10 mA, 30 kV |
| Slit Size[mm] | 0.6 |

Polarized Light Microscopy (PLM)

The presence of crystallinity (birefringence) was determined using an Olympus® BX50 polarizing microscope, equipped with a Motic® camera and image capture software (Motic® Images Plus 2.0). All images were recorded using the 20× objective, unless otherwise stated.

Thermogravimetric Analysis (TGA)

Approximately 5 mg of material was weighed into an open aluminum pan and loaded into a simultaneous thermogravimetric/differential thermal analyzer (TG/DTA) and held at room temperature. The sample was then heated at a rate of 10° C./minute from 25° C. to 300° C. during which time the change in sample weight was recorded along with any differential thermal events (DTA). Nitrogen was used as the purge gas, at a flow rate of 100 cm$^3$/minute.

Differential Scanning Calorimetry (DSC)

Approximately 5 mg of material was weighed into an aluminum DSC pan and sealed non-hermetically with a pierced aluminum lid. The sample pan was then loaded into a Seiko DSC6200 (equipped with a cooler) cooled and held at 25° C. Once a stable heat-flow response was obtained, the sample and reference were heated to about 240° C. at a scan rate of 10° C./minute and the resulting heat flow response monitored.

$^1$H Nuclear Magnetic Resonance (NMR)

$^1$H NMR studies were performed on a Bruker AV400 ($^1$H frequency: 400 MHz). $^1$H NMR studies of each sample were performed in DMSO-d6 or CDCl$_3$ and samples were prepared to about 10 mg/mL concentration.

Infrared Spectroscopy (IR)

Infrared spectroscopy was carried out on a Bruker ALPHA P spectrometer. Sufficient material was placed onto the center of the plate of the spectrometer and the spectra were obtained using the following parameters:

| Resolution: | 4 cm$^{-1}$ |
| Background Scan Time: | 16 scans |
| Sample Scan Time: | 16 scans |
| Data Collection: | 4000 to 400 cm$^{-1}$ |
| Result Spectrum: | Transmittance |
| Software: | OPUS version 6 |

Dynamic Vapor Sorption (DVS)

Approximately 10 mg of sample was placed into a glass vapor sorption balance pan and loaded into a DVS-1 dynamic vapor sorption balance by Surface Measurement Systems. The sample was subjected to a ramping profile from 0%-90% relative humidity (RH) at 10% increments, maintaining the sample at each step until a stable weight had been achieved (99.5% step completion). After completion of the sorption cycle, the sample was dried using the same procedure, from 90% RH down to 0% RH. The weight change during the sorption/desorption cycles were plotted, permitting the hygroscopic nature of the sample to be determined.

Karl Fischer Colometric Titration (KF)

About 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

High Performance Liquid Chromatography (HPLC)

| Instrument: | Agilent ® 110 |
| Column: | Waters Sunfire ™ C18 5 Qm, 150*4.6 mm |
| Flow Rate: | 1.0 mL/minute |
| Detection Wavelength: | 214 nm |
| Column Temperature: | 25° C. |
| Injection Volume: | 5 Q/mL |
| Mobile Phase A: | 0.03% TFA in water |
| Mobile Phase B (MPB): | 0.03% TFA in Acetonitrile |
| Standard/Sample Preparation: | 1 mg/mL in water |

| Gradient: | Time | % MPB |
|---|---|---|
| | 0 | 5 |
| | 16 | 95 |
| | 18 | 95 |

Ion Chromatography (IC)

| Instrument: | Thermo/Dionex ™ ED 40 |
| Electrochemical Detector, Autosampler, ASRS Utra 11 | P50 Gradient Pump, AS 1000 4 mm suppressor |
| Column: | Dionex ™ IonPac AG14A-5 Qm, 3 × 150 mm |
| Guard Column: | Dionex ™ IonPac AG14A-5 Qm, 3 × 30 mm |
| Mobile Phase: | 8 mM Na$_2$CO$_3$/1 mL NaHCO$_3$ |
| Flow Rate: | 0.5 mL/minute |
| Runtime: | 15 minutes |
| Detector suppression: | 50 µS, water regenerant as required |
| Column Temperature: | 30° C. |
| Injection Volume: | 25 µL (sample volume can be adjusted as required) |
| Standard Preparation: | 0.003 mg/mL in water | pKa Analysis

The potentiometric method parameters for pKa studies were developed by Absorption Systems® and were carried out as follows: three titrations in water with ionic strength adjusted to 0.15 with KCl (ISA water) were performed and the pH value ranged from 3.0 to 11.5.

Procedure:

The Compound titration was performed at 22° C. in ISA water. The weighed amount of TC (2.40 mg) was placed into a titration vial. ISA water (15 mL) was delivered automatically to the vial. The pH value of the solution was adjusted to 3 by adding 0.5 M HCl automatically. The titration with 0.5 M KOH was performed automatically until a pH value of 11.5 was reached. One additional mL of ISA water was added to the titration vial to perform the second titration and third titration, per titration respectively. The datasets for the three titrations were combined in the Refinement Pro program to create a Multiset for pKa calculation.

First, the pKa measurements and calculations for Compound C0105 were performed with the presumption that there were two basic ionizable groups. The lower value was found to be pH 1.5. Then the pKa calculations for the Compound were performed with the presumption that there was one basic ionizable group. The pKa values were found to be 8.0 and 1.5, as shown below for each amine nitrogen.

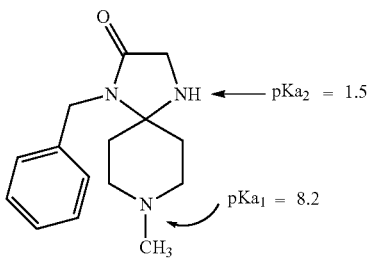 [SMILES: CN1CCC2(CC1)NCC(=O)N2Cc1ccccc1]

Assessment of HCl Mono-Salt Prepared

A. Stability Testing

Each salt formed was exposed to environments of 40° C./75% RH (open vial), elevated temperature (80° C., open vial) and ambient light (about 22° C. in a closed vial), for 1 week to assess both chemical and physical stability. Resulting solids were analyzed by X-ray powder diffraction (XRPD) to establish if any changes had occurred and by HPLC to determine purity.

B. Salt Disproportionation Studies

Each salt was slurried in water at room temperature (about 22° C.), with the excess solid taken at 1, 24 and 48 hours and analyzed by XRPD. The pH value of the supernatant was also monitored.

C. Hydration Studies

Slurries of each salt were created in IPA:water mixtures (95%:5%, 90%:10% and 60%:40% water) and stirred for about 48 hours at ambient temperature (about 22° C.). The resulting solid was then analyzed by XRPD to determine if any changes in crystal form had occurred on slurrying.

D. Thermodynamic Solubility Studies

Slurries of each salt (about 20 mg) were attempted to be created in different aqueous buffer media (PBS, FaSSIF, FeSSIF and SGF; Biorelevant.com) for about 48 hours at ambient temperature (about 22° C.). The resulting samples were found to be too soluble in the buffer media (>200 mg/mL) to carry out the study. See below for buffer compositions:

PBS 0.014 g of $KH_2PO_4$, 0.9 g of NaCl and 0.079 g $Na_2HPO_4$ anhydrous in 100 mL of de-ionized water.

Fasted-State Simulated Intestinal Fluid (FaSSIF)

0.021 g of NaOH, 0.198 g of $NaH_2PO_4$ (monohydrate), 0.309 g of NaCl and 0.112 g of SIF powder (Biorelevant.com Ltd, London, U.K.) in 0.050 mL of de-ionized water.

Fed-State Simulated Intestinal Fluid (FeSSIF)

0.202 g of NaOH, 0.433 g of glacial acetic acid, 0.594 g of NaCl and 0.560 g of SIF powder (Biorelevant.com Ltd, London, U.K.) in 0.050 mL of de-ionized water.

Simulated Gastric Fluid (SFG) 0.200 g of NaCl and 0.006 g of SIF powder (Biorelevant.com Ltd, London, U.K.) in 100 mL of de-ionized water.

Primary Polymorph Screen of HCl Di-Salt Hydrate

A. Temperature Cycling

To make efficient use of material, the samples recovered from solvent solubility screen were used also for the primary polymorph screen. If a suspension was obtained during solvent solubility screen, the mixture was used directly in the polymorph screen, whereas if a solution was obtained, more solid material was added in order to obtain a slurry. The suspensions were then temperature cycled between ambient temperature (about 22° C.) and 40° C. in 4 hour cycles for about 3 or 4 days (the cooling/heating rate after the 4 hour periods was about 1° C./minute). The mixtures were filtered and the recovered solids were permitted to dry at ambient conditions prior to analysis, whereas the mother liquors were retained for further studies.

B. Crash Cooling at 2° C. and −18° C.

Crash cooling studies were performed by placing saturated solutions of HCl di-salt in each of the 24 selected solvent systems, at about 2° C. If no solid material was recovered after 72 hours, the non-aqueous solutions were placed in a −18° C. environment for a minimum of 72 hours. Any solid material was then recovered and analyzed by XRPD and PLM.

C. Slow Evaporation

Slow evaporation studies were performed by permitting saturated solutions HCl di-salt to evaporate at ambient temperature (about 22° C.) and pressure. Any solid material was then recovered and analyzed by XRPD and PLM.

D. Anti-Solvent Addition at Ambient and 2° C.

Anti-solvent addition studies were conducted at ambient temperature (about 22° C.) by adding the selected anti-solvent (acetone or ethanol) to saturated solutions of HCl di-salt in each of the 24 selected solvent systems. Addition of anti-solvent was continued until there was no further precipitation or until no more anti-solvent could be added. Anti-solvent addition studies were also conducted at low temperature (2° C.) on the saturated solutions recovered from crash cooling experiments that did not produce any solid. Any solid material was recovered and analyzed quickly by PLM and XRPD in order to prevent form changes.

E. Scale-Up of HCl Di-Salt Hydrate Form 2

Approximately 0.6 mL of an acetone/water (20% Water) mixture was added to about 450 mg of the HCl di-salt (Form 1). The resulting slurry was temperature cycled between ambient temperature (about 22° C.) and 40° C. in 4 hour cycles for about 4 days. The solid was filtered and XRPD analysis was carried out before and after drying.

F. Scale-Up of HCl Di-Salt Hydrate Form 5

Approximately 20 mL of methanol was added to about 450 mg of the HCl di-salt (Form 1). The suspension obtained was stirred at 50° C. for approximately 3 hours and the resulting solution was filtered and permitted to evaporate at ambient temperature (about 22° C.). The gel/solid mixture obtained on evaporation was dried in vacuum and mixed with about 0.1 mL of methanol. The resulting slurry was temperature cycled between ambient temperature (about 22° C.) and 40° C. in 4 hour cycles for about one day. The recovered solid was filtered and analyzed by XRPD analysis before and after drying.

Full Physical Characterization of HCl Mono-Salt (FORM 1)

HPLC analysis indicated a purity of 98.8%.

Peak shift was observed by $^1$H-NMR analysis at high field when compared to free base, indicative of salt formation. Traces of IPA were also observed in the spectrum.

A 1:1 ratio was observed by IC analysis between the API and the chloride counter ion, suggesting mono salt formation.

TG/DT analysis showed a small weight loss of 0.2% below 180° C., followed by another small weight loss of about 0.5%, which corresponds to the endotherm observed in the DT trace at onset 184° C. Onset degradation occurs above 190° C.

KF analysis showed a water content of about 0.15%.

DSC analysis showed a large endotherm with an onset 180° C., which most likely corresponds to a melt.

DVS analysis indicated that the material is very hygroscopic above 70% RH. The sorption cycle indicated no significant mass increase until 60% RH (water uptake about 0.27%). A steady mass increase was observed between 60% and 70% RH (water uptake 2.55% at 70% RH) and a sharp mass increase between 70% and 90% RH (water uptake 68.57% at 90% RH). Desorption cycle indicated a steady mass decrease of 54.25% between 90% and 50% and another mass decrease of 6.10% between 10% and 0%. A hysteresis of 7.3% was observed at 0% RH. The material deliquesced at high RH.

Post-DVS XRPD analysis showed the material was not consistent with any of the forms previously observed before for the HCl mono-salt. This finding supports the observation that the material deliquesced during the analysis, and then re-crystallized to a new form upon drying.

Stability Studies (1 Week)

The results and observations for the stability studies of the HCl salt are reported in the table below.

No significant loss in purity was observed during stability studies by HPLC analysis.

XRPD analysis indicated that the material retained its polymorphic form during 1 week stability studies at ambient temperature and 80° C. The material deliquesced during 1 week at 40° C./75% RH, which is consistent with DVS analysis. A small loss in crystallinity was also observed during stability studies.

Results and Observations for 1 Week Stability Studies of HCl Mono-Salt

| Study | Observations T = 0 | HPLC Purity T = 0 | Conditions | Observations T = One week | HPLC Purity T = One week |
|---|---|---|---|---|---|
| 1 | White solid | 98.8% | Ambient | White solid | 98.6% |
| 2 | White solid | 98.8% | 40° C./75% RH | Clear liquid | 99.4% |
| 3 | White solid | 98.8% | 80° C. | Off-white solid | 99.5% |

Solvent Solubility Screen of HCl Mono-Salt

The results for the solvent solubility screen of the HCl mono-salt are reported in the table below. The screen indicates that the HCl mono-salt is poorly soluble in most of the selected solvent systems. However very high solubility was observed in methanol, 2-propanol:water (10%), acetone:water (20%) and water, and high solubility was observed in dimethylsulfoxide. Some solubility was also observed for dimethylacetamide, ethanol and acetone:water (5%).

Mono-HCl-Solubility Screen Results

| Solvent | Solubility at 40° C. (mg/mL) |
|---|---|
| Acetone | <10 |
| Acetonitrile | <10 |
| 2-Butanol | <10 |
| Cyclohexane | <10 |
| 1,2-Dichloroethene | <10 |
| Dimethylacetamide | about 10 |
| Dimethylsulfoxide | about 105 |
| Ethanol | about 20 |
| Ethyl acetate | <10 |
| Heptane | <10 |
| Isopropyl acetate | <10 |
| Methanol | >200 |
| Methyl acetate | <10 |
| Methyl ethyl ketone | <10 |
| Methyl isobutyl ketone | <10 |
| 2-MeTHF | <10 |
| 2-Propanol | <10 |
| 2-Propanol:water (10%) | >200 |
| tert-Butyl methyl ether | <10 |
| Tetrahydrofuran | <10 |
| Toluene | <10 |
| Acetone:Water (5%) | about 20 |
| Acetone:Water (20%) | >200 |
| Water | >200 |

Physical Characterisation of HCl Di-Salt Hydrate, Form 1

XRPD diffractogram indicated the material to be consistent with the di-salt obtained.

PLM analysis showed the material to be birefringent, between crossed polars, with block-like morphology.

HPLC analysis showed a purity of 99.1%.

$^1$H-NMR analysis indicated peak shift at high field, compared to the input material, indicative of salt formation. A small amount of solvent (2-propanol) was also observed in the spectrum. Furthermore, the spectrum is consistent with the analysis for the received HCl di-salt.

TG/DT analysis showed three consecutive weight losses <200° C., respectively of:
1) 5.4%, which corresponds to an endotherm in the DT trace at onset 81° C. (about 5.2% expected for the monohydrate);
2) 1.7%, which corresponds to an endotherm in the DT trace at onset 146° C.; and
3) 0.6%, which corresponds to an exotherm in the DT trace at peak 170° C.

Decomposition was observed >200° C.

A moisture content of about 5.5% was observed by KF analysis, which appeared consistent with TG analysis.

The material appeared to be hygroscopic above 50% RH by DVS analysis.

The sorption cycle indicated a small mass increase of about 0.56% between 0% and 50% RH, a steady mass increase between 50% and 80% (water uptake about 3.53% at 80% RH) and a sharp mass increase between 80% and 90% (water uptake about 8.26% at 90% RH).

Desorption cycle appeared to follow the same trend as the sorption between 90% and 70% RH, then a steady mass decrease of about 2.33% was observed between 70% and 0%.

A small hysteresis was observed throughout the humidity range. The largest hysteresis was observed at 50% RH where the difference in water uptake between the sorption and de-sorption profile was 0.78%. The final dry mass (at 0% RH following sorption and de-sorption profile) was observed to be 0.13% higher than the initial dry mass.

No significant differences in polymorphic form were observed after DVS by XRPD analysis.

HCl Di-Salt Hydrate, Form 1

Stability Studies (1 Week)

The results and observations for the stability studies of the HCl di-salt are reported in the table below.

HPLC analysis showed purities, respectively, of: 99.4% (ambient), 99.0% (40° C./75% RH) and 99.4% (80° C.).

No significant changes in polymorphic form were observed during stability studies of HCl di-salt Form 1 by XRPD analysis.

Results and Observations for 1 Week Stability Studies of HCl Di-Salt Hydrate-Form 1

| Study | Observations T = 0 | HPLC Purity T = 0 | Conditions | Observations T = One week | HPLC Purity T = One week |
|---|---|---|---|---|---|
| 1 | White solid | 99.1% | Ambient | White solid | 99.4% |
| 2 | White solid | 99.1% | 40° C./75% RH | White solid | 99.0% |
| 3 | White solid | 99.1% | 80° C. | Off-white solid | 99.4% |

Solvent Solubility Screen of HCl Di-Salt Hydrate, Form 1

The results for the solvent solubility screen of the HCl di-salt are reported in the table below. The screen indicates that the HCl di-salt is poorly soluble in most of the selected solvent systems, however very high solubility was observed in dimethylsulfoxide, and water. High solubility was also observed in acetone:water (20%). Moderate solubility was observed in 2-propanol:water (10%) and methanol.

Solubility Screen Results of HCl Di-Salt Hydrate-Form 1

| Solvent | Solubility at 40° C. (mg/mL) |
|---|---|
| Acetone | <10 |
| Acetonitrile | <10 |
| 2-Butanol | <10 |
| Cyclohexane | <10 |
| 1,2-Dichloroethene | <10 |
| Dimethylacetamide | <10 |
| Dimethylsulfoxide | >200 |
| Ethanol | <10 |
| Ethyl acetate | <10 |
| Heptane | <10 |
| Isopropyl acetate | <10 |
| Methanol | about 25 |
| Methyl acetate | <10 |
| Methyl ethyl ketone | <10 |
| Methyl isobutyl ketone | <10 |
| 2-MeTHF | <10 |
| 2-Propanol | <10 |
| 2-Propanol:water (10%) | about 25 |
| tert-Butyl methyl ether | <10 |
| Tetrahydrofuran | <10 |
| Toluene | <10 |
| Acetone:Water (5%) | <10 |
| Acetone:Water (20%) | about 85 |
| Water | >200 |

Primary Polymorph Screen of HCl Di-Salt Hydrate, Form 1

The results for the primary polymorph screen of HCl di-salt are summarized below in which Form 1 crystals were temperature cycled in the above solvents, the solvents were evaporated while containing the HCl di-salt, the solvent-HCl di-salt composition was crash cooled to 2° C. or crash cooled to −18° C., an anti-solvent was added at ambient temperature and added at 2° C.

Five crystal forms were identified, as well as an amorphous form that resulted from crash cooling to 2° C. from all solvents except those that contained added water, and dimethylacetamide.

Overall five polymorphic crystal forms were observed:

Form 1 (hydrate)—input material and observed from a large number of the studies;

Form 2 (hydrate);

Form 2 (phase pure)—temperature cycling in acetone:water (20%);

Form 2 (mixture)—temperature cycling in acetonitrile, acetone:water (10%) and 2-propanol:water (10%);

Form 3 (solvate)—temperature cycling in DMA;

Form 4—slow evaporation in heptane and toluene;

Form 5 (hydrate);

Form 5 (phase pure)—evaporation in methanol;

Form 5 (mixture)—evaporation in DMSO, 2-propanol and acetone:water (5%), crash cooling in water and anti-solvent addition in water.

Forms 1, 2 and 5 appeared to possess the highest levels of crystallinity and were selected for a secondary polymorph screen.

Polymorph Stability Studies of Form 1, Form 2 and Form 5

Approximately 20 mg of two of each of Form 1, Form 2 and Form 5 di-HCl salts were mixed together and suspended with the selected solvent systems, to obtain slurries. The resulting suspensions were each then stirred at different temperatures for about 3 days. A list containing the study details is tabulated in the table below. The recovered solids were filtered and analyzed by XRPD analysis to elucidate the predominant polymorph form recovered.

Table Polymorph Stability Studies

| Forms | Solvent | Solvent (µL) | Temperature |
|---|---|---|---|
| 1 + 2 | Methanol | 100 | Ambient* |
| 1 + 2 | IPA/water (10%) | 100 | Ambient* |
| 1 + 2 | Cyclohexane | 300 | Ambient* |
| 1 + 5 | Methanol | 80 | Ambient* |
| 1 + 5 | IPA/water (10%) | 80 | Ambient* |
| 1 + 5 | Cyclohexane | 200 | Ambient* |
| 2 + 5 | Methanol | 60 | Ambient* |
| 2 + 5 | IPA/water (10%) | 60 | Ambient* |
| 2 + 5 | Cyclohexane | 200 | Ambient* |
| 1 + 2 | Methanol | 60 | 60° C. |
| 1 + 2 | IPA/water (10%) | 60 | 60° C. |
| 1 + 2 | Cyclohexane | 200 | 60° C. |
| 1 + 5 | Methanol | 60 | 60° C. |
| 1 + 5 | IPA/water (10%) | 60 | 60° C. |
| 1 + 5 | Cyclohexane | 200 | 60° C. |
| 2 + 5 | Methanol | 60 | 60° C. |
| 2 + 5 | IPA/water (10%) | 60 | 60° C. |
| 2 + 5 | Cyclohexane | 200 | 60° C. |

*Ambient = about 22° C.

Polymorph Stability Studies of Form 1, Form 2 and Form 5

| Form | Solvent | T ° C. | Observations |
|---|---|---|---|
| 1 + 2 | Methanol | RT* | Form 2 (Tr# Form 1) |
| 1 + 2 | IPA/water (10%) | RT | Form 2 |
| 1 + 2 | Cyclohexane | RT | Form 1 + Form 2 |
| 1 + 5 | Methanol | RT | Form 5 |
| 1 + 5 | IPA/water (10%) | RT | Form 2 |
| 1 + 5 | Cyclohexane | RT | Form 1 (Tr Form 5) |
| 2 + 5 | Methanol | RT | Form 5 (Tr Form 2) |
| 2 + 5 | IPA/water (10%) | RT | Form 5 (Tr Form 2) |
| 2 + 5 | Cyclohexane | RT | Form 5 |
| 1 + 2 | Methanol | 60° C. | Form 5 (extra peaks) |
| 1 + 2 | IPA/water (10%) | 60° C. | Form 2 |
| 1 + 2 | Cyclohexane | 60° C. | Form 1 (Tr Form 2) |
| 1 + 5 | Methanol | 60° C. | Form 5 (extra peaks) |
| 1 + 5 | IPA/water (10%) | 60° C. | Form 5 |
| 1 + 5 | Cyclohexane | 60° C. | Form 1 (Tr Form 5) |
| 2 + 5 | Methanol | 60° C. | Form 5 (extra peaks) |
| 2 + 5 | IPA/water (10%) | 60° C. | Form 5 (extra peaks) |
| 2 + 5 | Cyclohexane | 60° C. | Form 5 (partially crystalline) |

Several studies were done using water as solvent, the compound is quite soluble in water. If a clear solution was obtained, Form 1 was formed by evaporation of the solvent or slow cooling. If not enough water is added, and therefore the slurry is not stirrable, no conversion into another polymorph was observed.

When an amount of water was added to obtain a good stirrable suspension, Form 2 is found. Cooling or evaporation of this suspension results in good crystalline Form 2. To obtain this suspension, only 0.8 volumes of water need to be added, 0.7 volumes gave a thick paste, whereas 1.0 volume results in a clear solution. Other water-miscible, solvents such as iso-propanol (IPA) can be mixed with the water to broaden the useful range of solvent to solid to provide the Form 2 polymorph.

Scale-up of Form 2 (10 g)

Scale-up was successful in reproducing Form 2 on a 10 g scale with 99.4% purity by HPLC.

However, some loss in crystallinity was observed upon drying. An improvement in crystallinity was observed during hydration studies, without change in polymorphic form, after DVS analysis and during stability studies at 40° C. and 75% RH, likely due to water uptake in the crystal lattice.

The material appeared less hygroscopic than Form 1 between 0% and 50% RH, but more hygroscopic than Form 1 by DVS analysis >50% RH: about 0.2% water uptake was observed at 50% RH and 24.9% was observed at 90% RH by DVS analysis (about 0.6% was observed for Form 1 at 50% RH and 8.3% was observed at 80% RH).

Form 2 was also found to be more sensitive to higher temperature than Form 1; a change in color (white to off-white/orange) and a purity of about 95.5% were observed by HPLC analysis after 1 week stability study at 80° C.

XRPD analysis indicated that Form 2 obtained from scale-up appeared consistent with the results originally seen. However, a loss in crystallinity was observed upon drying, which could be due the partial removal of water from the crystal lattice.

PLM analysis showed a plate/lathe-like morphology.

TG/DT analysis, indicated two consecutive weight losses of respectively: 0.7%, which corresponds to an endotherm in the DT trace at onset 70.5° C., and 4.8% (about 5.2% expected for the monohydrate), which corresponds to an endotherm in the DT trace at 128° C.

KF analysis showed a water content of about 6.1%.

DSC analysis showed a small endotherm at onset 76.9° C., likely due to unbound solvent (IPA or/and acetone), followed by a large and broad endotherm at 144.9° C., likely due to the loss of water, and a subsequent exotherm at 164.6° C.

The material appeared to be hygroscopic above 50% RH by DVS analysis.

The sorption cycle indicated no significant mass increase between 0% and 50% RH (water uptake about 0.2% at 50% RH), a steady mass increase was observed between 50% and 80% RH (water uptake about 9.9% at 80% RH) and a sharp mass increase between 80% and 90% RH (water uptake about 24.9% at 90% RH).

The desorption cycle appeared to follow the same trend as the sorption cycle between 90% and 70% and then a gradual mass decrease of 6.77% was observed between 70% and 0%.

A small hysteresis (i.e. retention of moisture) of about 0.4% RH was observed at 0% RH on desorption.

Post-DVS XRPD analysis showed an increase in crystallinity compared to the dry input material, which could be due the re-introduction of water into the crystal lattice and subsequent crystallization of some of the amorphous content.

A purity of 99.4% was observed by HPLC analysis.

IC analysis showed an API:hyrdrochloride ratio of about 1:2, as expected for the HCl di-salt.

The $^1$H-NMR spectrum of Form 2, showed some extra peaks compared to Form 1, in particular, a multiplet at δ: 8.91, the broad singlet at δ: 8.14 and the three doublets at δ:4.35, 3.61 and 2.84.

FT-IR analysis was obtained as a reference.

Stability Studies (1 Week)

HPLC analysis showed purities of: 99.5% (ambient), 99.8% (40° C./75% RH) and 95.5% (80° C.). A color change (white to off-white/orange) was also observed for the sample stored at 80° C., which is consistent with the lower purity (95.5%). Both observations, the color change and the loss of purity, indicate that Form 2 is more sensitive to elevated temperatures compared to Form 1, although Form 2 appears more stable at ambient temperatures.

XRPD analysis did not indicate significant changes in polymorphic form during stability studies of HCl di-salt hydrate Form 2, at both ambient and 80° C. However, an increase in crystallinity was observed at 40° C./75% RH (likely due to water up-take in the crystal lattice and subsequent crystallization of some amorphous content).

Results and Observations for 1 Week Stability Studies of HCl Di-Salt

| Study | Observations T = 0 | HPLC Purity | Conditions | Observations T = One week | HPLC Purity |
|---|---|---|---|---|---|
| 1 | White solid | 99.4% | Ambient | White solid | 99.5% |
| 2 | White solid | 99.4% | 40° C./75% RH | White solid | 99.8% |
| 3 | White solid | 99.4% | 80° C. | Orange solid | 95.5% |

Hydration Studies

The results and observation for the hydration studies of the HCl di-salt (Form 2) are reported in the table below.

XRPD analysis indicated that no form change occurred on stirring in the various IPA/water mixtures for 24 hours, which indicated no higher hydrate formation. An improvement in the crystallinity was observed compared to the dry input material, likely due to water up-take in the crystal lattice.

Results of Observations for Hydration Studies of HCl Di-Salt Hydrate (Form 2)

| Study | Water % | Water activity (approx.) | Total volume IPA/water (mL) | Observations |
|---|---|---|---|---|
| 1 | 40 | 0.9 | 20 | White suspension |
| 2 | 10 | 0.7 | 60 | White suspension |
| 3 | 5 | 0.5 | 100 | White suspension |

The articles "a" and "an" are used herein to refer to one or to more than one (i.e., to at least one) of the grammatical object of the article. By way of example, "an element" means one element or more than one element.

The foregoing description and the examples are intended as illustrative and are not to be taken as limiting. Still other variations within the spirit and scope of this invention are possible and will readily present themselves to those skilled in the art.

The invention claimed is:

1. A solid-state form of the compound of Formula III selected from

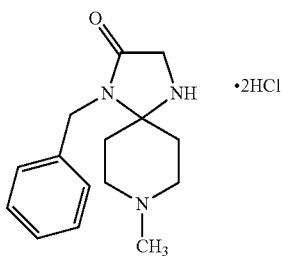

(a) crystalline 1-benzyl-8-methyl-1,4,8-triazaspiro-[4.5]-decan-2-one dihydrochloride monohydrate, Crystalline monohydrate Form 1;
(b) crystalline 1-benzyl-8-methyl-1,4,8-triazaspiro-[4.5]-decan-2-one dihydrochloride monohydrate, Crystalline monohydrate Form 2;
(c) crystalline 1-benzyl-8-methyl-1,4,8-triazaspiro-[4.5]-decan-2-one dihydrochloride dimethylacetamide solvate, Crystalline dimethylacetamide solvate Form 3;
(d) amorphous 1-benzyl-8-methyl-1,4,8-triazaspiro-[4.5]-decan-2-one dihydrochloride, Amorphous Form 4; and
(e) crystalline 1-benzyl-8-methyl-1,4,8-triazaspiro-[4.5]-decan-2-one dihydrochloride monohydrate, Crystalline monohydrate Form 5.

2. A crystalline form of the compound of Formula III according to claim 1 selected from
(a) Crystalline monohydrate Form 1, 1-benzyl-8-methyl-1,4,8-triazaspiro-[4.5]-decan-2-one dihydrochloride monohydrate characterized by:
an X-ray powder diffraction pattern having at least 1 peak selected from 8.0, 13.0, 13.8, 19.1 and 20.2 2θ±0.2° 2θ; or
an X-ray powder diffraction pattern substantially similar to FIG. 1;
(b) Crystalline monohydrate Form 2, 1-benzyl-8-methyl-1,4,8-triazaspiro-[4.5]-decan-2-one dihydrochloride monohydrate characterized by:
an X-ray powder diffraction pattern having at least 1 peak selected from 9.9, 11.9, 13.2, 14.2, 15.8, 20.0 and 20.4 2θ±0.2° 2θ; or
an X-ray powder diffraction pattern substantially similar to FIG. 2;
(c) Crystalline dimethylacetamide solvate Form 3, 1-benzyl-8-methyl-1,4,8-triazaspiro-[4.5]-decan-2-one dihydrochloride dimethylacetamide solvate characterized by:
an X-ray powder diffraction pattern having a peak at 5.5 2θ±0.2° 2θ; or
an X-ray powder diffraction pattern substantially similar to FIG. 3;
(d) amorphous Form 4, 1-benzyl-8-methyl-1,4,8-triazaspiro-[4.5]-decan-2-one dihydrochloride characterized by:
an X-ray powder diffraction pattern substantially similar to FIG. 4; and (e) Crystalline monohydrate Form 5, 1-benzyl-8-methyl-1,4,8-triazaspiro-[4.5]-decan-2-one dihydrochloride monohydrate characterized by:
an X-ray powder diffraction pattern having a peak at 22.4 2θ±0.2° 2θ; or
an X-ray powder diffraction pattern substantially similar to FIG. 5.

3. A crystalline form of the compound of Formula II selected from

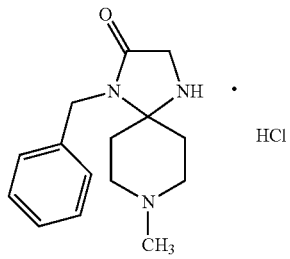

(a) crystalline 1-benzyl-8-methyl-1,4,8-triazaspiro-[4.5]-decan-2-one monohydrochloride, Crystalline Form 1;
(b) crystalline 1-benzyl-8-methyl-1,4,8-triazaspiro-[4.5]-decan-2-one monohydrochloride, Crystalline Form 2;
(c) crystalline 1-benzyl-8-methyl-1,4,8-triazaspiro-[4.5]-decan-2-one monohydrochloride, Crystalline Form 3; and
(d) crystalline 1-benzyl-8-methyl-1,4,8-triazaspiro-[4.5]-decan-2-one monohydrochloride, Crystalline Form 4.

4. A crystalline form of the compound of Formula II according to claim 3 selected from (a) crystalline 1-benzyl-8-methyl-1,4,8-triazaspiro-[4.5]-decan-2-one monohydrochloride, Crystalline Form 1, characterized by:
an X-ray powder diffraction pattern having at least one peak selected from 12.4, 20.5, 21.7 and 25.5 2θ±0.2° 2θ; or
an X-ray powder diffraction pattern substantially similar to FIG. 6;
(b) crystalline 1-benzyl-8-methyl-1,4,8-triazaspiro-[4.5]-decan-2-one monohydrochloride, Crystalline Form 2, characterized by:
an X-ray powder diffraction pattern having at least one peak selected form 10.5, 13.8 and 22.7 2θ±0.2° 2θ; or
an X-ray powder diffraction pattern substantially similar to FIG. 7;
(c) crystalline 1-benzyl-8-methyl-1,4,8-triazaspiro-[4.5]-decan-2-one monohydrochloride, Crystalline Form 3, characterized by:
an X-ray powder diffraction pattern having at least one peak selected from 13.6, 15.8, 20.8, 22.0 and 27.2 2θ±0.2° 2θ; or
an X-ray powder diffraction pattern substantially similar to FIG. 8; and
(d) crystalline 1-benzyl-8-methyl-1,4,8-triazaspiro-[4.5]-decan-2-one monohydrochloride, Crystalline Form 4, characterized by:
an X-ray powder diffraction pattern having at lease one peak selected from 11.2, 18.0 and 20.0 2θ±0.2° 2θ; or
an X-ray powder diffraction pattern substantially similar to FIG. 9.

5. A crystalline form of the compound of Formula I that is selected from

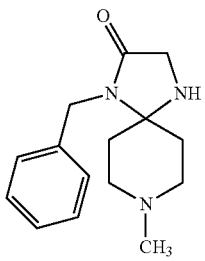

(a) crystalline 1-benzyl-8-methyl-1,4,8-triazaspiro-[4.5]-decan-2-one free base, Crystalline Form 1;
(b) crystalline 1-benzyl-8-methyl-1,4,8-triazaspiro-[4.5]-decan-2-one free base, Crystalline Form 2; and
(c) crystalline 1-benzyl-8-methyl-1,4,8-triazaspiro-[4.5]-decan-2-one free base, Crystalline Form 3.

6. A crystalline form of the compound of Formula I according to claim 5 selected from
(a) crystalline 1-benzyl-8-methyl-1,4,8-triazaspiro-[4.5]-decan-2-one free base, Crystalline Form 1, characterized by:
an X-ray powder diffraction pattern having at least one peak selected from 24.1, 26.3 and 27.3 2θ±0.2° 2θ; or
an X-ray powder diffraction pattern substantially similar to FIG. 10;
(b) crystalline 1-benzyl-8-methyl-1,4,8-triazaspiro-[4.5]-decan-2-one free base, Crystalline Form 2, characterized by:
an X-ray powder diffraction pattern having at least one peak selected from 13.1 and 16.8 2θ±0.2° 2θ; or
an X-ray powder diffraction pattern substantially similar to FIG. 11; and
(c) crystalline 1-benzyl-8-methyl-1,4,8-triazaspiro-[4.5]-decan-2-one free base, Crystalline Form 3, characterized by:
an X-ray powder diffraction pattern having at least one peak selected from 10.1, 14.1 and 19.3 2θ±0.2° 2θ; or
an X-ray powder diffraction pattern substantially similar to FIG. 12.

7. The crystalline or amorphous compound according to claim 1 dissolved or dispersed in a pharmaceutical composition.

8. The crystalline compound according to claim 3 dissolved or dispersed in a pharmaceutical composition.

9. The crystalline compound according to claim 5 dissolved or dispersed in a pharmaceutical composition.

* * * * *